US009663515B2

(12) United States Patent
Claremon et al.

(10) Patent No.: US 9,663,515 B2
(45) Date of Patent: *May 30, 2017

(54) DIHYDROPYRROLOPYRIDINE INHIBITORS OF ROR-GAMMA

(71) Applicant: Vitae Pharmaceuticals, Inc., Fort Washington, PA (US)

(72) Inventors: David A. Claremon, Maple Glen, PA (US); Lawrence Wayne Dillard, Yardley, PA (US); Chengguo Dong, Staten Island, NY (US); Yi Fan, Doylestown, PA (US); Stephen D. Lotesta, Burlington, NJ (US); Andrew Marcus, Media, PA (US); Suresh B. Singh, Kendall Park, NJ (US); Colin M. Tice, Maple Glen, PA (US); Jing Yuan, Lansdale, PA (US); Wei Zhao, Germantown, MD (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/933,524

(22) Filed: Nov. 5, 2015

(65) Prior Publication Data

US 2016/0122345 A1 May 5, 2016

Related U.S. Application Data

(60) Provisional application No. 62/075,602, filed on Nov. 5, 2014.

(51) Int. Cl.
C07D 471/04 (2006.01)
(52) U.S. Cl.
CPC ................... *C07D 471/04* (2013.01)
(58) Field of Classification Search
None
See application file for complete search history.

(56) References Cited

U.S. PATENT DOCUMENTS

| | | | |
|---|---|---|---|
| 5,238,950 A | 8/1993 | Clader et al. | |
| 5,272,158 A | 12/1993 | Hartman et al. | |
| 5,326,760 A | 7/1994 | McElroy et al. | |
| 5,364,869 A | 11/1994 | De | |
| 5,389,631 A | 2/1995 | Claremon et al. | |
| 5,571,774 A | 11/1996 | Hamprecht et al. | |
| 5,719,144 A | 2/1998 | Hartman et al. | |
| 5,770,590 A | 6/1998 | Natsugari et al. | |
| 5,786,352 A | 7/1998 | Natsugari et al. | |
| 6,103,659 A | 8/2000 | Pasenok et al. | |
| 6,177,443 B1 | 1/2001 | Madsen et al. | |
| 6,417,207 B1 | 7/2002 | Garvey et al. | |
| 6,444,617 B1 | 9/2002 | Takaishi et al. | |
| 6,489,315 B1 | 12/2002 | Natsugari et al. | |
| 6,512,117 B1 | 1/2003 | Harclerode et al. | |
| 6,770,666 B2 | 8/2004 | Hashimoto et al. | |
| 7,112,600 B1 | 9/2006 | Hashimoto et al. | |
| 7,115,752 B2 | 10/2006 | Lesieur et al. | |
| 7,183,318 B2 | 2/2007 | Lesieur et al. | |
| 7,244,730 B2 | 7/2007 | Suzuki et al. | |
| 7,732,616 B2 | 6/2010 | Marlow et al. | |
| 7,750,021 B2 | 7/2010 | Mi et al. | |
| 8,389,739 B1 | 3/2013 | Thacher et al. | |
| 8,415,351 B2 | 4/2013 | Wagner et al. | |
| 9,266,886 B2 * | 2/2016 | Lotesta | C07D 471/04 |
| 2002/0132817 A1 | 9/2002 | Natsugari et al. | |
| 2003/0050320 A1 | 3/2003 | Hashimoto et al. | |
| 2004/0002424 A1 | 1/2004 | Minn et al. | |
| 2004/0038973 A1 | 2/2004 | Nahra et al. | |
| 2005/0004204 A1 | 1/2005 | Suzuki et al. | |
| 2005/0020593 A1 | 1/2005 | Mailliet et al. | |

(Continued)

FOREIGN PATENT DOCUMENTS

| | | |
|---|---|---|
| CA | 2031684 A1 | 6/1991 |
| CA | 2134192 A1 | 5/1995 |

(Continued)

OTHER PUBLICATIONS

Babu "Emerging therapeutic strategies in COPD" Drug Discovery Today vol. 20, No. 3 Mar. 2015 371.*
Sangshetti "Antileishmanial drug discovery: comprehensive review of the last 10 years" RSC Adv., 2015, 5, 32376-32415.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
"ICD-9-CM Tabular List of Diseases (FY03)" on the Washington University School of Medicine in St. Louis website Online "http://gamma.wustl.edu/division/icd9tbp.pdf" accessed Sep. 10, 2015.*
Flowers "How we treat chronic graft-versus-host disease" Blood, Jan. 22, 2015 x vol. 125, No. 4 606-615.*
Chaichian "Targeted Therapies in Systemic Lupus Erythematosus: A State-of-the-Art Review" J Clin Cell Immunol 2013, S6, 1-8.*
Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.*

(Continued)

*Primary Examiner* — David K O'Dell
(74) *Attorney, Agent, or Firm* — McCarter & English, LLP; Steven G. Davis; Michael J. DeGrazia

(57) ABSTRACT

Provided are novel compounds of Formula (I):

$$Cy^2\text{-structure-}C(=O)\text{-}NH\text{-}C(R^7)(R^8)\text{-}Cy^1 \quad (I)$$

pharmaceutically acceptable salts thereof, and pharmaceutical compositions thereof, which are useful in the treatment of diseases and disorders mediated by RORγ. Also provided are pharmaceutical compositions comprising the novel compounds of Formula (I) and methods for their use in treating one or more inflammatory, metabolic, autoimmune and other diseases or disorders.

15 Claims, No Drawings

(56) References Cited

U.S. PATENT DOCUMENTS

| | | |
|---|---|---|
| 2005/0234065 A1 | 10/2005 | Hulin et al. |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |

FOREIGN PATENT DOCUMENTS

| | | | |
|---|---|---|---|
| CA | 2352612 | A1 | 6/2000 |
| CA | 2524027 | A1 | 12/2004 |
| CN | 1424770 | A | 6/2003 |
| CN | 1869036 | A | 11/2006 |
| CN | 101225070 | A | 7/2008 |
| CN | 101455661 | A | 6/2009 |
| CN | 102180780 | A | 9/2011 |
| DE | 4343922 | A1 | 6/1995 |
| DE | 4446396 | A1 | 7/1995 |
| EP | 254951 | A2 | 2/1988 |
| EP | 321368 | A1 | 6/1989 |
| EP | 468187 | A2 | 1/1992 |
| EP | 520277 | A2 | 12/1992 |
| EP | 520573 | A1 | 12/1992 |
| EP | 540334 | A1 | 5/1993 |
| EP | 655439 | A2 | 5/1995 |
| EP | 733632 | A1 | 9/1996 |
| EP | 1178048 | A1 | 2/2002 |
| FR | 2725946 | A1 | 4/1996 |
| FR | 2926554 | A1 | 7/2009 |
| GB | 2276384 | A | 9/1994 |
| JP | H06236056 | A | 8/1994 |
| JP | H1143489 | A | 2/1999 |
| JP | 2000007661 | A | 1/2000 |
| JP | 2003/171380 | A | 6/2003 |
| JP | 2003531894 | A | 10/2003 |
| JP | 2004203791 | A | 7/2004 |
| WO | 90/09787 | A1 | 9/1990 |
| WO | 94/00119 | A1 | 1/1994 |
| WO | 94/24712 | A1 | 10/1994 |
| WO | 95/11680 | A1 | 5/1995 |
| WO | 95/17397 | A1 | 6/1995 |
| WO | 96/26187 | A1 | 8/1996 |
| WO | 97/32832 | A1 | 9/1997 |
| WO | 98/40385 | A1 | 9/1998 |
| WO | 98/42666 | A1 | 10/1998 |
| WO | 99/47132 | A2 | 9/1999 |
| WO | 99/58495 | A1 | 11/1999 |
| WO | 99/58496 | A1 | 11/1999 |
| WO | 00/32192 | A1 | 6/2000 |
| WO | 00/67754 | A1 | 11/2000 |
| WO | 01/05790 | A1 | 1/2001 |
| WO | 01/47883 | A1 | 7/2001 |
| WO | 01/51128 | A1 | 7/2001 |
| WO | 01/83445 | A1 | 11/2001 |
| WO | 01/85722 | A1 | 11/2001 |
| WO | 02/24650 | A2 | 3/2002 |
| WO | 02/38107 | A2 | 5/2002 |
| WO | 02/081443 | A1 | 10/2002 |
| WO | 02/081447 | A1 | 10/2002 |
| WO | 02/081463 | A1 | 10/2002 |
| WO | 02/085855 | A1 | 10/2002 |
| WO | 03/008421 | A1 | 1/2003 |
| WO | 03/029252 | A1 | 4/2003 |
| WO | 03/029254 | A1 | 4/2003 |
| WO | 03/070710 | A1 | 8/2003 |
| WO | 03/076440 | A1 | 9/2003 |
| WO | 03/104216 | A1 | 12/2003 |
| WO | 2004/014365 | A1 | 2/2004 |
| WO | 2004/042029 | A2 | 5/2004 |
| WO | 2004/065351 | A1 | 8/2004 |
| WO | 2004/089897 | A1 | 10/2004 |
| WO | 2004/103309 | A2 | 12/2004 |
| WO | 2004/108133 | A2 | 12/2004 |
| WO | 2004/111010 | A1 | 12/2004 |
| WO | 2004/113330 | A1 | 12/2004 |
| WO | 2005/005392 | A1 | 1/2005 |
| WO | 2005/011601 | A2 | 2/2005 |
| WO | 2005/023806 | A2 | 3/2005 |
| WO | 2005/025504 | A2 | 3/2005 |
| WO | 2005/028480 | A2 | 3/2005 |
| WO | 2005/039564 | A1 | 5/2005 |
| WO | 2005/051301 | A2 | 6/2005 |
| WO | 2005/060958 | A1 | 7/2005 |
| WO | 2005/063296 | A2 | 7/2005 |
| WO | 2005/100334 | A1 | 10/2005 |
| WO | 2006/032631 | A1 | 3/2006 |
| WO | 2006/062981 | A1 | 6/2006 |
| WO | 2006/065842 | A2 | 6/2006 |
| WO | 2006/074428 | A2 | 7/2006 |
| WO | 2006/082001 | A1 | 8/2006 |
| WO | 2006/092731 | A1 | 9/2006 |
| WO | 2006/109085 | A1 | 10/2006 |
| WO | 2007/007054 | A1 | 1/2007 |
| WO | 2007/036733 | A1 | 4/2007 |
| WO | 2007/036734 | A1 | 4/2007 |
| WO | 2007/050124 | A1 | 5/2007 |
| WO | 2007/084451 | A1 | 7/2007 |
| WO | 2007/084455 | A1 | 7/2007 |
| WO | 2007/097931 | A2 | 8/2007 |
| WO | 2007/101224 | A2 | 9/2007 |
| WO | 2007/107545 | A1 | 9/2007 |
| WO | 2007/109596 | A2 | 9/2007 |
| WO | 2007/131982 | A2 | 11/2007 |
| WO | 2008/013963 | A2 | 1/2008 |
| WO | 2008/044027 | A1 | 4/2008 |
| WO | 2008/044029 | A1 | 4/2008 |
| WO | 2008/044041 | A1 | 4/2008 |
| WO | 2008/044045 | A1 | 4/2008 |
| WO | 2008/044054 | A2 | 4/2008 |
| WO | 2008/048991 | A1 | 4/2008 |
| WO | 2008/073865 | A2 | 6/2008 |
| WO | 2008/083070 | A1 | 7/2008 |
| WO | 2008/086161 | A1 | 7/2008 |
| WO | 2008/132155 | A2 | 11/2008 |
| WO | 2008/135524 | A2 | 11/2008 |
| WO | 2008/135526 | A1 | 11/2008 |
| WO | 2008/149163 | A2 | 12/2008 |
| WO | 2009/004496 | A2 | 1/2009 |
| WO | 2009/013299 | A2 | 1/2009 |
| WO | 2009/026248 | A2 | 2/2009 |
| WO | 2009/050228 | A2 | 4/2009 |
| WO | 2009/052319 | A1 | 4/2009 |
| WO | 2009/052320 | A1 | 4/2009 |
| WO | 2009/068463 | A2 | 6/2009 |
| WO | 2009/073788 | A1 | 6/2009 |
| WO | 2009/097972 | A1 | 8/2009 |
| WO | 2009/112445 | A1 | 9/2009 |
| WO | 2009/112678 | A2 | 9/2009 |
| WO | 2009/112826 | A1 | 9/2009 |
| WO | 2009/112839 | A1 | 9/2009 |
| WO | 2009/124755 | A1 | 10/2009 |
| WO | 2009/131926 | A1 | 10/2009 |
| WO | 2009/144450 | A1 | 12/2009 |
| WO | 2010/003022 | A1 | 1/2010 |
| WO | 2010/021878 | A1 | 2/2010 |
| WO | 2010/033350 | A1 | 3/2010 |

(56) References Cited

FOREIGN PATENT DOCUMENTS

| | | |
|---|---|---|
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/062938 A1 | 4/2014 |
| WO | 2014/086894 A1 | 6/2014 |
| WO | WO 2015116904 A1 * | 8/2015 ........... C07D 471/04 |
| WO | WO 2016061160 A1 * | 4/2016 |

OTHER PUBLICATIONS

Lim "Age-related macular degeneration" The Lancet vol. 379 May 5, 2012, pp. 1728-1738.*
Edwards et. al. Molecular genetics of AMD and current animal models. Angiogenesis 2007 10:119-132.*
Campochiaro "The Complexity of Animal Model Generation for Complex Diseases" JAMA, Feb. 17, 2010—vol. 303, No. 7 657-658.*
Healthline Online "http://www.healthline.com/health/inflammatory-bowel-disease", accessed Sep. 9, 2015 Inflammatory Bowel Disease.*
Vickers "The utility of animal models to evaluate novel anti-obesity agents" British Journal of Pharmacology (2011) 164 1248-1262.*
Lutz "Overview of Animal Models of Obesity" Curr Protoc Pharmacol. Sep. 2012 ; Chapter: Unit 5.61. 1-22.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Galie et. al. "Guidelines for the diagnosis and treatment of pulmonary hypertension" European Heart Journal (2009) 30, 2493-2537.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Elborn "Cystic fibrosis" The Lancet, Published online Apr. 29, 2016 Online "http://dx.doi.org/10.1016/S0140-6736(16)00576-6" 1-13.*
Georg Pilz, "Modern multiple sclerosis treatment—what is approved, what is on the horizon" Drug Discovery Today Dec. 2008, vol. 13, Nos. 23/24 1013-1025.*
Chapter XI in Psoriasis and Psoriatic Arthritis: An Integrated Approach Kenneth B. Gordon Eric M. and Ruderman Editors Springer-Verlag Berlin Heidelberg 2005, p. 134-181.*
Cyr "Recent progress on nuclear receptor RORc modulators" Bioorganic & Medicinal Chemistry Letters 26 (2016) 4387-4393.*
Schlecker, et al., "Regioselective Monometalation of 2,5-Pyridinedicarboxamides with (2,2,6,6-Tetramethylpiperidino) magnesium Chloride (TMPMgCl)," Liebigs Annalen, 1995, vol. 8, pp. 1441-1446.
Marcoux, et al., "Annulation of Ketones with Vinamidinium Hexafluorophosphate Salts: An Efficient Preparation of Trisubstituted Pyridines," Organic Letters, 2000, vol. 2, No. 15, 2339-2341.
Schlecker, et al., "Regioselective Metalation of Pyridinylcarbamates and Pyridinecarboxamides with (2,2,6,6-Tetramethylpiperidino)magnesium Chloride," J. Org. Chem., 1995, 60, 8414-8416.
Maddur et al., "Biology, Pathogenesis of Automimmune and Inflammatory Diseases, and Therapeutic Strategies", The American Journal of Pathology, 181(1):8-18 (2012).

* cited by examiner

DIHYDROPYRROLOPYRIDINE INHIBITORS OF ROR-GAMMA

RELATED APPLICATIONS

This application claims the benefit of U.S. Provisional Application No. 62/075,602, filed Nov. 5, 2014, the entire contents of which is incorporated herein by reference.

TECHNICAL FIELD OF THE INVENTION

The present invention is directed to novel retinoic acid receptor-related orphan receptor gamma ("RORγ" or "ROR-gamma") inhibitors, processes for their preparation, pharmaceutical compositions containing these inhibitors, and their use in the treatment of inflammatory, metabolic, autoimmune and other diseases mediated by RORγ.

BACKGROUND OF THE INVENTION

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertns-tert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY OF THE INVENTION

It has now been found that compounds described herein, and pharmaceutically acceptable compositions thereof, are effective inhibitors of RORγ (see e.g., Table 2). Such compounds include those of Formula (I):

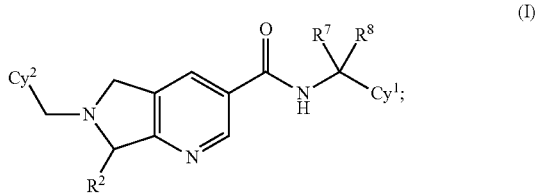

or a pharmaceutically acceptable salt thereof, wherein each of $R^2$, $R^7$, $R^8$, $Cy^1$, and $Cy^2$ are as defined and described herein.

The provided compounds, and pharmaceutically acceptable compositions thereof, are inverse agonists or antagonists of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

Compounds provided herein possess the technical advantage of having therapeutic relevance in cell-free competition assays, cell-based transcriptional assays, whole blood assays, and hERG potassium channel assays, e.g., see Tables 2 and 3 below.

DETAILED DESCRIPTION OF CERTAIN EMBODIMENTS

1. General Description of Compounds of the Invention

In certain embodiments, the present invention provides a compound of Formula (I):

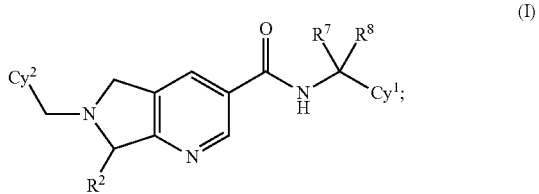

or a pharmaceutically acceptable salt thereof, wherein:

$R^2$ is $(C_1-C_3)$alkyl, hydroxy$(C_1-C_3)$alkyl, halo$(C_1-C_3)$alkyl, benzyl, $(C_1-C_3)$alkoxy$(C_1-C_3)$alkyl, tetrahydropyranyl, or —$CH_2$-tetrahydropyranyl;

$Cy^1$ is phenyl or pyridyl, each substituted with $(C_1-C_3)$alkylsulfonyl;

$Cy^2$ is cyclohexyl or tetrahydropyranyl, each optionally substituted with one or more groups selected from halo and halo$(C_1-C_3)$alkyl;

$R^7$ is hydrogen, $(C_1-C_3)$alkyl-O—$(C_1-C_3)$alkyl, aminocarbonyl-O—$(C_1-C_3)$alkyl, $(C_1-C_3)$alkylaminocarbonyl-O—$(C_1-C_3)$alkyl, di$(C_1-C_3)$alkylaminocarbonyl-O—$(C_1-C_3)$alkyl, or hydroxycarbonyl$(C_1-C_3)$alkyl-O—$(C_1-C_3)$alkyl; and $R^8$ is $(C_1-C_3)$alkyl-O—$(C_1-C_3)$alkyl, aminocarbonyl-O—$(C_1-C_3)$alkyl, $(C_1-C_3)$alkylaminocarbonyl-O—$(C_1-C_3)$alkyl, di$(C_1-C_3)$alkylaminocarbonyl-O—$(C_1-C_3)$alkyl, or hydroxycarbonyl$(C_1-C_3)$alkyl-O—$(C_1-C_3)$alkyl.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-6 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, iodine, and bromine.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or all geometric isomers.

The compounds of the invention may be prepared as individual enantiomers by either enantio-specific synthesis or resolved from an enantiomerically enriched mixture.

Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g, the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

The compounds of the invention may be present in the form of pharmaceutically acceptable salts. For use in medicines, the salts of the compounds of the invention refer to nontoxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present invention provides a compound of Formula (I),

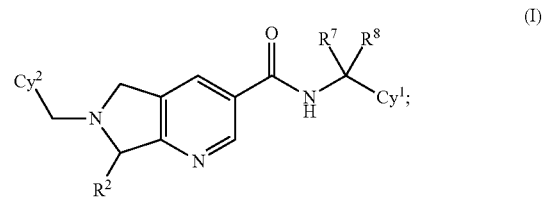

or a pharmaceutically acceptable salt thereof, wherein the variables are as described above.

In a second embodiment, the compound of Formula (I) is of Formula (II):

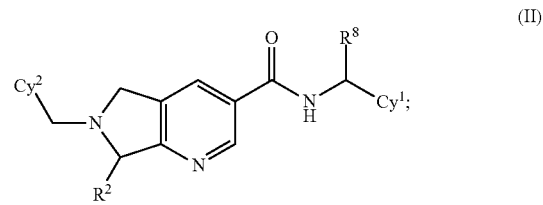

or a pharmaceutically acceptable salt thereof, wherein the variables in structural Formula (II) are as described for Formula (I).

In a third embodiment, the compound of Formula (I) is of Formula (III):

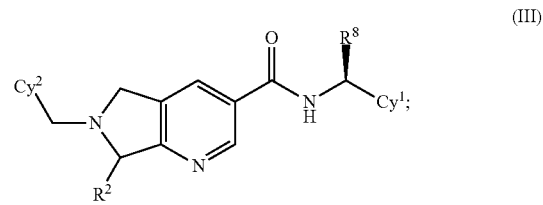

or a pharmaceutically acceptable salt thereof, wherein the variables in structural Formula (III) are as described for Formula (I).

In a fourth embodiment, the compound of Formula (I) is of Formula (IV):

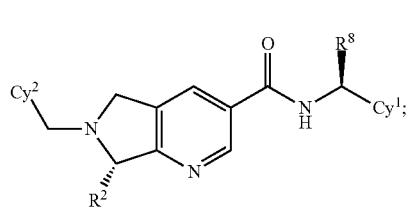

(IV)

or a pharmaceutically acceptable salt thereof, wherein the variables in structural Formula (IV) are as described for Formula (I).

In a fifth embodiment, $R^2$ in Formulas (I) to (IV) is $(C_1$-$C_3)$alkyl, wherein the remaining variables are as described for Formula (I).

In a sixth embodiment, $Cy^2$ in Formulas (I) to (IV) is cyclohexyl or tetrahydropyranyl, each substituted with halo$(C_1$-$C_3)$alkyl, wherein the remaining variables are as described for Formula (I) or the fifth embodiment.

In a seventh embodiment, the compound of Formula (I) is of Formula (V):

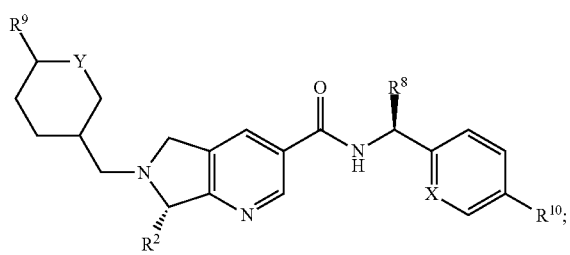

(V)

or a pharmaceutically acceptable salt thereof, wherein X is CH or N; Y is O or $CH_2$; $R^9$ is halo$(C_1$-$C_3)$alkyl; and $R^{10}$ is $(C_1$-$C_3)$alkylsulfonyl, wherein the remaining variables are as described for Formula (I) or the fifth or sixth embodiment.

In an eighth embodiment, the compound of Formula (I) is of Formula (VI):

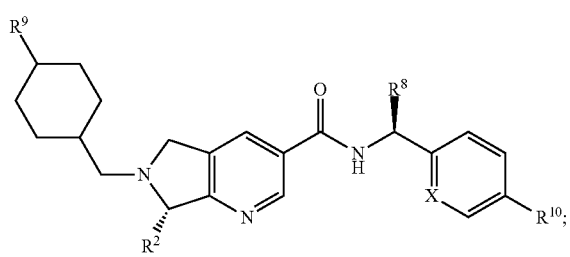

(VI)

or a pharmaceutically acceptable salt thereof, wherein the variables in structural Formula (VI) are as described for Formula (I), or the fifth, sixth, or seventh embodiment.

In a ninth embodiment, the compound of Formula (I) is of Formula (VII):

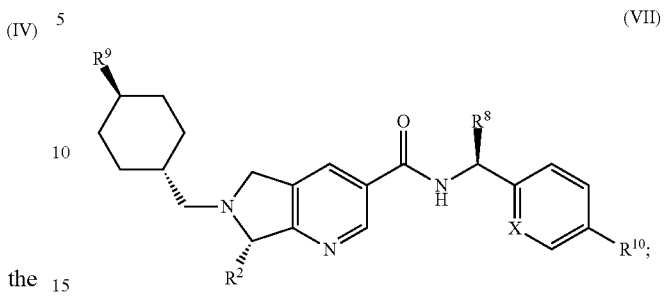

(VII)

or a pharmaceutically acceptable salt thereof, wherein the variables in structural Formula (VII) are as described for Formula (I), or the fifth, sixth, or seventh embodiment.

In a tenth embodiment, $R^9$ in Formulas (I) to (VII) is $CF_3$; and $R^{10}$ is $SO_2Et$ or $SO_2Me$, wherein the remainder of the variables are as described for Formula (I), or the fifth, sixth, or seventh embodiment.

In an eleventh embodiment, $R^8$ in Formulas (I) to (VII) is —$CH_2OCH_3$, —$CH_2OCH_2CH_3$, —$CH_2OC(O)NH_2$, or —$CH_2OCH_2COOH$, wherein the remainder of the variables are as described for Formula (I), or the fifth, sixth, seventh, or tenth embodiment. Alternatively, $R^8$ in Formulas (I) to (VII) is —$CH_2OCH$, wherein the remainder of the variables are as described for Formula (I), or the fifth, sixth, seventh, or tenth embodiment.

In a twelfth embodiment, the compound of Formula (I) is of Formula (VIII):

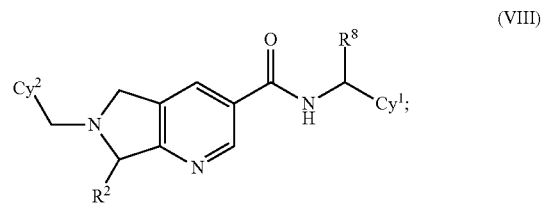

(VIII)

or a pharmaceutically acceptable salt thereof, wherein
$R^2$ is $(C_1$-$C_3)$alkyl;
$Cy^1$ is phenyl or pyridyl, each substituted with $(C_1$-$C_3)$alkylsulfonyl;
$Cy^2$ is cyclohexyl or tetrahydropyranyl, each substituted with halo$(C_1$-$C_3)$alkyl; and
$R^8$ is $(C_1$-$C_3)$alkyl-O—$(C_1$-$C_3)$alkyl.

In a thirteenth embodiment, the compound of Formula (I) is of Formula (IX):

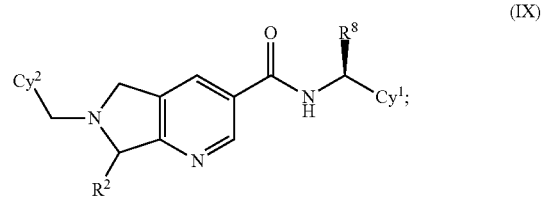

(IX)

or a pharmaceutically acceptable salt thereof, wherein the variables in structural Formula (IX) are as described for Formula (VIII).

In a fourteenth embodiment, the compound of Formula (I) is of Formula (X):

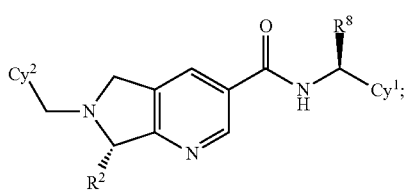

or a pharmaceutically acceptable salt thereof, wherein the variables in structural Formula (X) are as described for Formula (VIII).

In a fifteenth embodiment, $Cy^1$ in Formulas (VIII) to (X) is phenyl substituted with $(C_1-C_3)$alkylsulfonyl; and $Cy^2$ is cyclohexyl substituted with halo$(C_1-C_3)$alkyl, wherein the remaining variables are as described in Formula (VIII). Alternatively, $Cy^1$ in Formulas (VIII) to (X) is phenyl substituted with —$SO_2Et$ or —$SO_2Me$; and $Cy^2$ is cyclohexyl substituted with $CF_3$, wherein the remaining variables are as described in Formula (VIII).

In a sixteenth embodiment, $R^2$ in Formulas (VIII) to (X) is ethyl or isopropyl, wherein the remaining variables are as described in Formula (VIII) or the fifteenth embodiment.

Specific examples of compounds of the invention are provided in the EXEMPLIFICATION. Pharmaceutically acceptable salts as well as the neutral forms of these compounds are included in the invention.

In certain embodiments, the present invention provides any one of the compounds in the foregoing examples, or a pharmaceutically acceptable salt thereof.

In certain embodiments, the present invention provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a subject (e.g., a human) with a disorder mediated by RORγ using a composition comprising a compound of the invention and a pharmaceutically acceptable carrier, adjuvant, or vehicle. In certain embodiments, the amount of compound of the invention in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of RORγ. Thus, in some embodiments, the present invention provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Diseases and conditions treatable according to the methods of the invention include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, urticaria, hives, angioedema, cystic fibrosis, allograft rejection, multiple sclerosis, Balo's concentric (circular) sclerosis, Balo disease, leukoencephalitis periaxialis concentrica, encephalitis periaxialis concentrica, scleroderma, limited scleroderma, CREST syndrome, arthritis, rheumatoid arthritis, juvenile rheumatoid arthritis, reactive arthritis, Reiter's syndrome, osteoarthritis, ankylosing spondylitis, systemic lupus erythematosus (SLE), psoriasis, plaque psoriasis, guttate psoriasis, inverse psoriasis, pustular psoriasis, erythrodermic psoriasis, psoriatic epidermal hyperplasia, epidermal hyperplasia, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyositis, graft versus host disease, chronic graft versus host disease, acute graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, celiac sprue, neuromyelitis, juvenile idiopathic arthritis, systemic sclerosis, myocardial infarction, pulmonary hypertension, osteoarthritis, cutaneous leishmaniasis, sinonasal polyposis, cancer, including but not limited to lung cancer, gastric cancer, breast cancer and colon cancer, thrombocytopenic purpura, idiopathic thrombocytopenic purpura (ITP), immune thrombocytopenic purpura, cartilage inflammation, bone degradation, vasculitis, acute disseminated encephalomyelitis (ADEM), acute necrotizing hemorrhagic leukoencephalitis, Addison's disease, agammaglobulinemia, alopecia areata, amyloidosis, anti-glomerular basement membrane (GBM) nephritis, anti-tubular basement membrane (TBM) nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, axonal and neuronal neuropathies, bullous pemphigoid, cardiomyopathy, Castleman disease, Chagas disease, chronic inflammatory demyelinating polyneuropathy (CIDP), chronic recurrent multifocal ostomyelitis (CRMO), Churg-Strauss syndrome, cicatricial pemphigoid, benign mucosal pemphigoid, Cogan's syndrome, cold agglutinin disease, congenital heart block, coxsackie myocarditis, essential mixed cryoglobulinemia, demyelinating neuropathies, dermatitis herpetiformis, Devic's disease, neuromyelitis optica, discoid lupus, Dressler's syndrome, eosinophilic esophagitis, eosinophilic fasciitis, erythema nodosum, experimental allergic encephalomyelitis, Evans syndrome, fibrosing alveolitis, giant cell arteritis, temporal arteritis, giant cell myocarditis, glomerulonephritis, Goodpasture's syndrome, granulomatosis with polyangiitis (GPA), Wegener's granulomatosis, Hashimoto's encephalitis, Hashimoto's thyroiditis, hemolytic anemia, Henoch-Schonlein purpura, herpes gestationis, hypogammaglobulinemia, IgA nephropathy, IgG4-related sclerosing disease, immunoregulatory lipoproteins, inclusion body myositis, interstitial cystitis, juvenile myositis, Kawasaki syndrome, Lambert-Eaton syndrome, leukocytoclastic vasculitis, lichen planus, lichen sclerosus, ligneous conjunctivitis, linear IgA disease (LAD), chronic Lyme disease, Meniere's disease, microscopic polyangiitis, mixed connective tissue disease (MCTD), Mooren's ulcer, Mucha-Habermann disease, myositis, narcolepsy, neuromyelitis optica, Devic's syndrome, neutropenia, ocular cicatricial pemphigoid, optic neuritis, palindromic rheumatism, pediatric autoimmune neuropsychiatric disorders associated with *streptococcus* (PANDAS), paraneoplastic cerebellar degeneration, paroxysmal nocturnal hemoglobinuria (PNH), Parry-Romberg syndrome, Parsonnage-Turner syndrome, pars planitis, peripheral uveitis, pemphigus, peripheral neuropathy, perivenous encephalomyelitis, pernicious anemia, POEMS syndrome, polyarteritis nodosa, type I autoimmune polyglandular syndrome, type II autoimmune polyglandular syndrome, type III autoimmune polyglandular syndrome, polymyalgia rheumatic, postmyocardial infarction syndrome, postpericardiotomy syndrome, progesterone dermatitis, primary biliary cirrhosis, primary sclerosing cholangitis, idiopathic pulmonary fibrosis, pyoderma gangrenosum, pure red cell aplasia, Raynaud's phenomenon, reflex sympathetic dystrophy, relapsing polychondritis, restless legs syndrome, retroperitoneal fibrosis, rheumatic fever, rheumatoid arthritis, sarcoidosis, Schmidt syndrome, sperm autoimmunity, stiff person syndrome, subacute bacterial endocarditis (SBE), Susac's syndrome, sympathetic ophthalmia, Takayasu's arteritis, temporal arteritis, giant cell arteritistesticular autoimmunity, Tolosa-Hunt syndrome, transverse myelitis, undifferentiated connective tissue disease (UCTD), vesiculobullous dermatosis, and vitiligo.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's and other central nervous system (CNS) disorders associated with altered sleep and/or circadian rhythms.

In one embodiment, a human patient is treated with a compound of the invention and a pharmaceutically acceptable carrier, adjuvant, or vehicle, wherein said compound is present in an amount to treat or ameliorate one or more of the diseases and conditions recited above. In another embodiment, the diseases and conditions treated or ameliorated by a compound of the invention include, e.g., asthma, COPD, bronchitis, allergic rhinitis, atopic dermatitis, contact dermatitis, acne, urticaria, cystic fibrosis, allograft rejection, multiple sclerosis, scleroderma, arthritis, rheumatoid arthritis, juvenile rheumatoid arthritis, osteoarthritis, ankylosing spondylitis, SLE, psoriasis, Hashimoto's disease, pancreatitis, autoimmune diabetes, type I diabetes, autoimmune ocular disease, ulcerative colitis, Crohn's disease, regional enteritis, IBD, IBS, Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, PsA, steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, OSAS, Behçet's disease, dermatomyositis, polymyocitis, graft versus host disease, primary biliary cirrhosis, liver fibrosis, NAFLD, sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer. In an alternative embodiment, the diseases and conditions treated or ameliorated by a compound of the invention include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, SLE, scleroderma, psoriasis, PsA, steroid resistant asthma and rheumatoid arthritis in the patient.

The invention further relates to a combination therapy for treating or ameliorating a disease or a disorder described herein. In some embodiments, the combination therapy comprises administering at least one compound of the invention in combination with one or more agents for treating or ameliorating inflammatory, metabolic and autoimmune diseases or disorders mediated by RORγ. In some embodiments, the combination therapy comprises administering at least one compound of the invention in combination with one or more agents for treating or ameliorating a disease or a disorder described herein. In some embodiments, the combination therapy comprises administering at least one compound of the invention in combination with one or more agents for the treatment of diseases including asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, SLE, scleroderma, psoriasis, PsA, steroid resistant asthma and rheumatoid arthritis.

The compounds according to the invention may also be used in combination with immunotherapies for the treatment of a disease or disorder disclosed herein.

Combination therapy includes, e.g., co-administration of a compound of the invention and one or more other agents, sequential administration of a compound of the invention and one or more other agents, administration of a composition containing a compound of the invention and one or more other agents, or simultaneous administration of separate compositions containing a compound of the invention and one or more other agents.

The invention further provides a method of treating a subject, such as a human, suffering from one of the above-mentioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthesis

The compounds of the present invention can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, 2$^{nd}$ edition, John Wiley & Sons, 1991, and Richard Larock, Comprehensive Organic Transformations, 4$^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
|---|---|
| ACN, MeCN, CH$_3$CN | acetonitrile |
| AIBN | azobisisobutyronitrile |
| aq | aqueous |
| Boc | tert-butoxycarbonyl or t-butoxycarbonyl |
| brine | saturated aqueous NaCl |
| Cbz | benzyloxy carbonyl |
| Cpd | compound |
| DCM or CH$_2$Cl$_2$ | methylene chloride |
| DIEA | diisopropyl ethyl amine |
| DMF | dimethyl formamide |
| DMS/Me$_2$S | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| Et$_2$O | ethyl ether |
| Et$_3$SiH | triethylsilane |
| Et$_3$N | triethylamine |
| EtOAc, EA, AcOEt | ethyl acetate |
| EtOH | ethanol |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| H$_2$O$_2$ | hydrogen peroxide |
| HPLC | high performance liquid chromatography |
| i-BuOCOCl | iso-butoxycarbonyl chloride |
| ICl | iodochloride |
| K$_3$PO$_4$ | tripotassium phosphate |
| LC-MS | liquid chromatography-mass spectrometry |
| LDA | lithium diiisopropylamide |
| MCPBA, m-CPBA | meta-chloroperoxybenzoic acid |
| MeOH | methanol |
| MeI | methyl iodide |
| Me | methyl |
| mg | milligram |
| min | minute(s) |

-continued

| Abbreviation | Meaning |
|---|---|
| mL | milliliters |
| mmol | millimoles |
| mp, m.p. | melting point |
| MS | mass spectrometry |
| MW, uwave | microwave |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| PdCl$_2$dppf | [1,1-bis(diphenylphosphino)ferrocene]dichloropalladium(ii) |
| Pd$_2$(dba)$_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| Ti(OEt)$_4$ | titanium tetra ethoxide |

Compounds according to Formula (I), can be prepared by reacting an intermediate compound of Formula (500) with an alkyl or benzyl halide, according to reaction Scheme 1, a reaction that is performed in a polar aprotic solvent, such as, for example, acetonitrile, in the presence of a suitable base, such as, for example, N,N-diisopropylethylamine or potassium carbonate. Alternatively, the final compounds according to Formula (I), can be prepared by reacting an intermediate compound of Formula (500) with an aldehyde, according to reaction Scheme 1, following art-known reductive amination procedure, in the typical solvent, such as, for example, dichloroethane, dichloromethane, or methanol; in the presence of suitable reducing reagent, such as sodium cyanoborohydride or sodium triacetoxyborohydride. In reaction Scheme 1, all variables are defined as in Formula (I) and G$^1$ is a leaving group, such as, for example, bromide, chloride, mesylate (methanesulfonate), tosylate (p-toluenesulfonate), trifluoromethanesulfonate (triflate), or iodide.

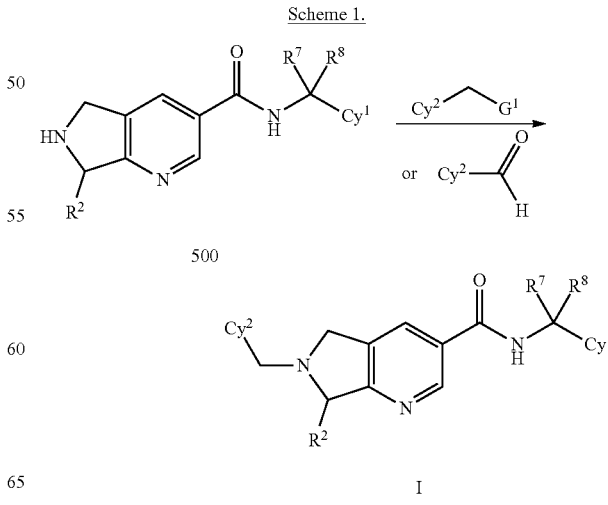

Scheme 1.

Intermediate compound of Formula (500) can be can be prepared by deprotecting an intermediate compound of Formula (501), wherein Pg is a suitable nitrogen protecting group (Greene and Wuts, Protective Groups in Organic Synthesis, $2^{nd}$ edition, John Wiley & Sons, 1991), e.g., Pg=tert-butylcarbamate, removed with trifluoroacetic acid according to Scheme 2. In reaction Scheme 2, all variables are defined as in Formula (I).

Scheme 2.

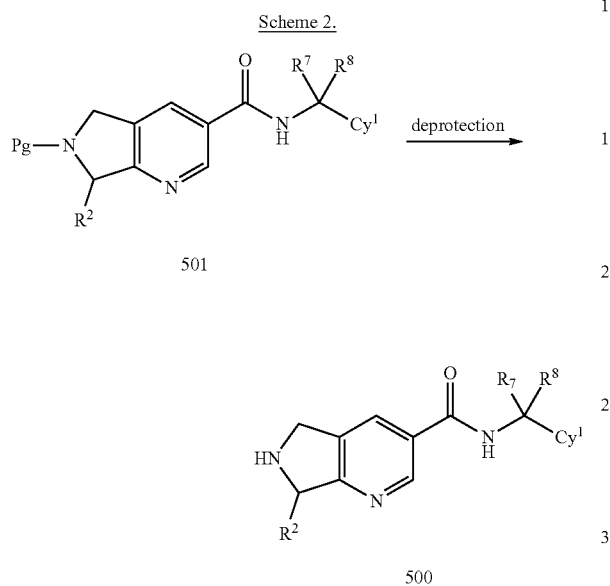

501

500

Intermediate compound of Formula (501) can be prepared from a carboxylic acid (502) and an amine (503), according to Scheme 3. The reaction is conveniently carried out in the presence of an activating reagent, for example, N-(3-Dimethylaminopropyl)-N'-ethylcarbodiimide hydrochloride (EDCI) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0 to 60° C.

Scheme 3.

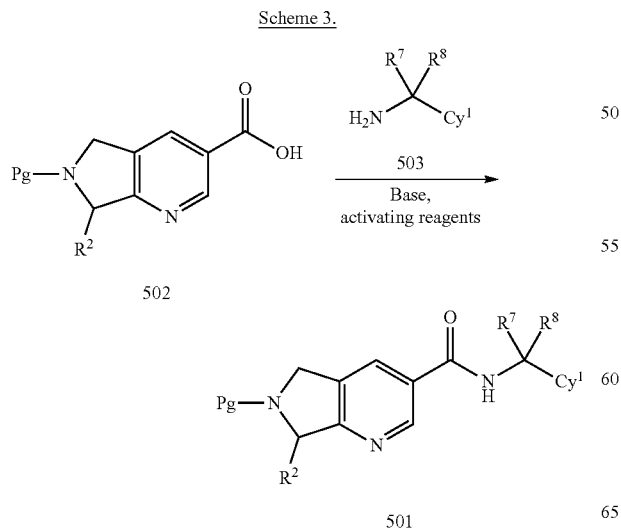

502

501

Preparation of Intermediates

Preparation A1: tert-butyl (S)-3-chloro-7-isopropyl-5,7-dihydro-6H-pyrrolo[3,4-b]pyridine-6-carboxylate

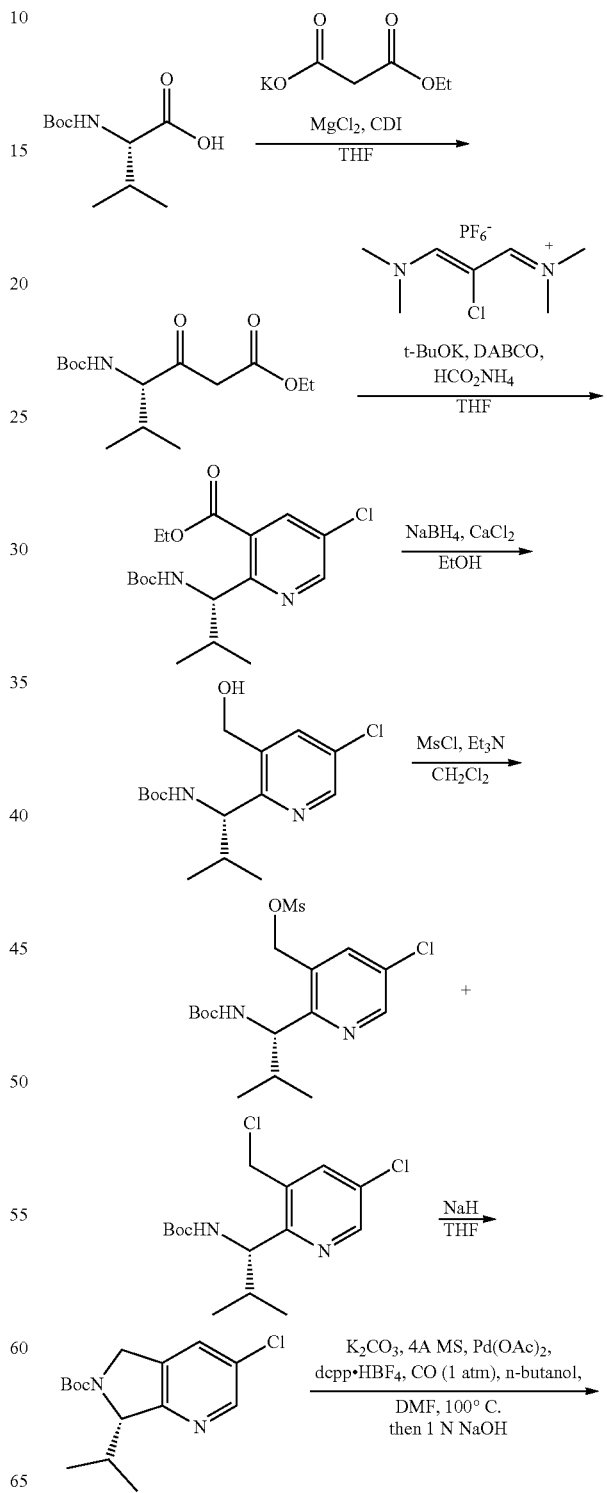

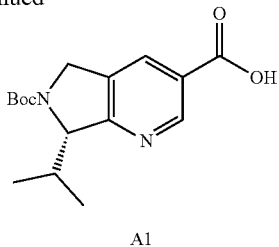

A1

Step 1: ethyl (S)-4-((tert-butoxycarbonyl)amino)-5-methyl-3-oxohexanoate

To a stirred solution of Boc-Val-OH (3.11 g, 14.3 mmol) in THF (40 mL) at rt was added 1,1'-carbonyldiimidazole (3.48 g, 21.5 mmol). The mixture was stirred at rt for 1 h, then magnesium chloride (1.36 g, 14.3 mmol) and ethyl potassium malonate (2.44 g, 14.3 mmol) were added successively. The mixture was then heated to 50° C. and stirred for 15 h. The mixture was cooled to rt and quenched with 1 N HCl (100 mL). The aqueous phase was extracted with EtOAc (3×100 mL), then the combined organic layer was washed with brine (50 mL). The organic layer was dried over anhydrous MgSO$_4$, filtered and concentrated under reduced pressure. The residue was purified by silica gel chromatography (eluting with 5% EtOAc in hexanes) to afford ethyl (S)-4-((tert-butoxycarbonyl)amino)-5-methyl-3-oxohexanoate (3.53 g, 86% yield) as a yellow oil. LC-MS $t_R$=0.91 min in 1 min chromatography, MS (ESI) m/z 288.3 [M+H]$^+$. $^1$H NMR (CDCl$_3$, 400 MHz): δ 5.08 (d, J=8.4 Hz, 1H), 4.33 (dd, J=4.4 Hz, 8.8 Hz, 1H), 4.20 (q, J=7.2 Hz, 2H), 3.54 (s, 2H), 2.27-2.17 (m, 1H), 1.44 (s, 9H), 1.27 (t, J=7.2 Hz, 3H), 1.01 (d, J=6.8 Hz, 3H), 0.82 (d, J=6.8 Hz, 3H).

Step 2: (S)-2-(1-((tert-butoxycarbonyl)amino)-2-methylpropyl)-5-chloronicotinate To a mixture of ethyl (S)-4-((tert-butoxycarbonyl)amino)-5-methyl-3-oxohexanoate (9.68 g, 33.7 mmol) from above in THF (100 mL) at 0° C. was added potassium tert-butoxide (3.78 g, 35.4 mmol). The mixture was warmed to rt and stirred for 45 min, at which point 1,4-diazabicyclo[2.2.2]octane (3.78 g, 33.7 mmol) and 2-chloro-1,3-bis(dimethylamino)trimethinium hexaflurophosphate (15.5 g, 50.5 mmol) were added successively. The mixture was heated to 45° C. and stirred for 3 h, at which point ammonium acetate (5.19 g, 67.4 mmol) was added. The mixture was then heated to reflux and stirred for 15 h. It was then cooled to rt and concentrated under reduced pressure. The residue was dry-loaded onto a silica gel column and purified (eluting with 5% EtOAc in hexanes, gradient to 15%) to yield 6.09 g of ethyl (S)-2-(1-((tert-butoxycarbonyl)amino)-2-methylpropyl)-5-chloronicotinate (51%). LC-MS $t_R$=1.14 min in 1 min chromatography, MS (ESI) m/z 357.3 [M+H]$^+$. $^1$H NMR (CDCl$_3$, 400 MHz): δ 8.61 (d, J=2.4 Hz, 1H), 8.18 (d, J=2.8 Hz, 1H), 5.71 (d, J=9.6 Hz, 1H), 5.62 (dd, J=5.2 Hz, 9.6 Hz, 1H), 4.42 (q, J=7.2 Hz, 2H), 2.08-2.00 (m, 1H), 1.42 (s, 9H), 1.42 (t, J=7.2 Hz, 3H), 0.93 (d, J=6.4 Hz, 3H), 0.83 (d, J=6.4 Hz, 3H).

Step 3: tert-butyl (S)-(1-(5-chloro-3-(hydroxymethyl)pyridin-2-yl)-2-methylpropyl)carbamate To a stirred solution of ethyl (S)-2-(1-((tert-butoxycarbonyl)amino)-2-methylpropyl)-5-chloronicotinate (6.09 g, 17.1 mmol) at 0° C. in EtOH (70 mL) was added sodium borohydride (1.30 g, 34.1 mmol). Calcium chloride (1.89 g, 17.1 mmol) was added portionwise while maintaining the temperature between 0° C. and 5° C. The resulting mixture was stirred at 0° C. for 90 min, then quenched slowly at 0° C. with saturated aqueous ammonium chloride solution (100 mL). The aqueous phase was extracted with EtOAc (3×100 mL), then the combined organic layer was washed with brine (50 mL), dried over anhydrous MgSO$_4$, filtered and concentrated under reduced pressure. Crude tert-butyl (S)-(1-(5-chloro-3-(hydroxymethyl)pyridin-2-yl)-2-methylpropyl)carbamate was carried forward without any purification. LC-MS $t_R$=0.94 min in 1 min chromatography, MS (ESI) m/z 315.3 [M+H]$^+$. $^1$H NMR (CDCl$_3$, 400 MHz): δ 8.46 (d, J=2.4 Hz, 1H), 7.67 (d, J=2.8 Hz, 1H), 5.34 (d, J=9.2 Hz, 1H), 4.99 (dd, J=2.0 Hz, 8.4 Hz, 1H), 4.54 (t, J=9.2 Hz, 1H), 4.41 (dd, J=10.0 Hz, 12.4 Hz, 1H), 4.33 (d, J=10.0 Hz, 1H), 2.18-2.12 (m, 1H), 1.36 (s, 9H), 1.10 (d, J=6.4 Hz, 3H), 0.69 (d, J=6.8 Hz, 3H).

Step 4: (S)-(2-(1-((tert-butoxycarbonyl)amino)-2-methylpropyl)-5-chloropyridin-3-yl)methyl methanesulfonate To a solution of tert-butyl (S)-(1-(5-chloro-3-(hydroxymethyl)pyridin-2-yl)-2-methylpropyl)carbamate (5.33 g, 16.9 mmol) in CH$_2$Cl$_2$ (70 mL) at 0° C. was added triethylamine (3.54 mL, 25.4 mmol) and methanesulfonyl chloride (1.44 mL, 18.6 mmol). The mixture was warmed to rt and stirred for 3 h, at which point it was quenched with saturated aqueous sodium bicarbonate solution (100 mL). The aqueous phase was extracted with ethyl acetate (3×100 mL). The combined organic layer was washed with brine (50 mL), dried over anhydrous MgSO$_4$, filtered and concentrated under reduced pressure. The crude residue (a 3:1 mixture of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate) was carried forward without any purification. LC-MS $t_R$=1.01 min in 1 min chromatography, MS (ESI) m/z 393.3 [M+H]$^+$. $^1$H NMR (CDCl$_3$, 400 MHz): δ 8.53 (d, J=2.4 Hz, 1H), 7.74 (d, J=2.8 Hz, 1H), 5.44 (d, J=12.4 Hz, 1H), 5.37 (d, J=12.8 Hz, 1H), 5.31 (d, J=8.4 Hz, 1H), 4.59 (t, J=9.2 Hz, 1H), 3.13 (s, 3H), 2.13-2.04 (m, 1H), 1.36 (s, 9H), 1.03 (d, J=6.8 Hz, 3H), 0.77 (d, J=6.8 Hz, 3H). Characterization data from a purified sample of (S)-(2-(1-((tert-butoxycarbonyl)amino)-2-methylpropyl)-5-chloropyridin-3-yl)methyl methanesulfonate.

Step 5: tert-butyl (S)-3-chloro-7-isopropyl-5,7-dihydro-6H-pyrrolo[3,4-b]pyridine-6-carboxylate To a solution of (S)-(2-(1-((tert-butoxycarbonyl)amino)-2-methylpropyl)-5-chloropyridin-3-yl)methyl methanesulfonate and tert-butyl (S)-(1-(5-chloro-3-(chloromethyl)pyridin-2-yl)-2-methylpropyl)carbamate (3:1 mixture, 6.39 g, 16.9 mmol) in THF (75 mL) at 0° C. was added sodium hydride (60% dispersion in mineral oil, 811 mg, 20.3 mmol). The mixture was warmed to rt and stirred for 15 h, at which point it was quenched with saturated aqueous ammonium chloride solution (100 mL). The aqueous phase was extracted with ethyl acetate (3×100 mL). The combined organic layer was washed with brine (50 mL), dried over anhydrous MgSO$_4$, filtered and concentrated under reduced pressure. The residue was purified by silica gel chromatography (eluting with 5% EtOAc in hexanes, gradient to 10%) to give tert-butyl (S)-3-chloro-7-isopropyl-5,7-dihydro-6H- pyrrolo[3,4-b]pyridine-6-carboxylate (4.31 g, 85% yield over 3 steps) as a yellow oil. LC-MS $t_R$=1.12 min in 1 min chromatography, MS (ESI) m/z 297.3 [M+H]$^+$. $^1$H NMR (CDCl$_3$, 400 MHz, mixture of rotamers): δ 8.43 (s, 1H), 7.56 (s, 0.6H), 7.50 (s, 0.4H), 4.96 (s, 0.4H), 4.87 (s, 0.6H), 4.86 (d, J=16.0 Hz, 0.6H), 4.74 (d, J=15.6 Hz, 0.4H), 4.52 (d, J=12.0 Hz, 0.4H), 4.49 (d, J=15.2 Hz, 0.6H), 2.60-2.51 (m, 0.4H), 2.40-2.36 (m, 0.6H), 1.49 (s, 9H), 1.08 (d, J=7.2 Hz, 1.2H), 0.99 (d, J=7.2 Hz, 1.8H), 0.78 (d, J=6.8 Hz, 1.8H), 0.72 (d, J=6.8 Hz, 1.2H).

Step 6: tert-butyl (S)-3-chloro-7-isopropyl-5,7-dihydro-6H-pyrrolo[3,4-b]pyridine-6-carboxylate Potassium carbonate (758 mg, 5.49 mmol) and 4 Å molecular sieves (250 mg) were placed in a 50 mL round-bottom flask which was then flame dried. Palladium (II) acetate (32.8 mg, 146 μmol) and 1,3-bis(dicyclohexylphosphonium)propane bis (tetrafluoroborate) (179 mg, 292 μmol) were added to the flask, which was then sealed with a septum. Tert-butyl (S)-3-chloro-7-isopropyl-5,7-dihydro-6H-pyrrolo[3,4-b]pyridine-6-carboxylate (1.09 g, 3.66 mmol) was dissolved in DMF (12 mL) and added to the flask, followed by 1-butanol (3.34 mL, 36.6 mmol). The flask was then evacuated and backfilled with CO three times, with the final time under a balloon of 1 atm of CO. The flask was heated to 100° C. and stirred for 6 h. The mixture was then cooled to rt and quenched with 1 N NaOH (25 mL). The mixture was stirred for 30 min, at which point isopropyl acetate (50 mL) was added. The phases were separated, then the organic phase was extracted with 1 N NaOH (2×50 mL), then the combined aqueous layer was acidified to pH=2 with concentrated HCl. The aqueous layer was then extracted with EtOAc (3×25 mL), then the combined organic layer was dried over anhydrous MgSO$_4$, filtered and concentrated under reduced pressure. The crude residue (S)-6-(tert-butoxycarbonyl)-7-isopropyl-6,7-dihydro-5H-pyrrolo[3,4-b]pyridine-3-carboxylic acid was carried forward without any purification.

Preparation A2: (S)-6-(tert-butoxycarbonyl)-7-ethyl-6,7-dihydro-5H-pyrrolo[3,4-b]pyridine-3-carboxylic acid

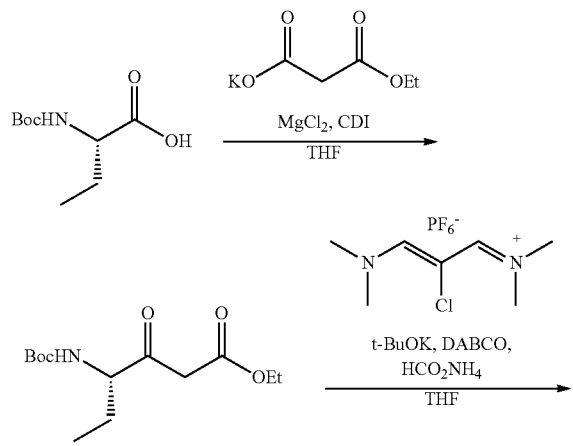

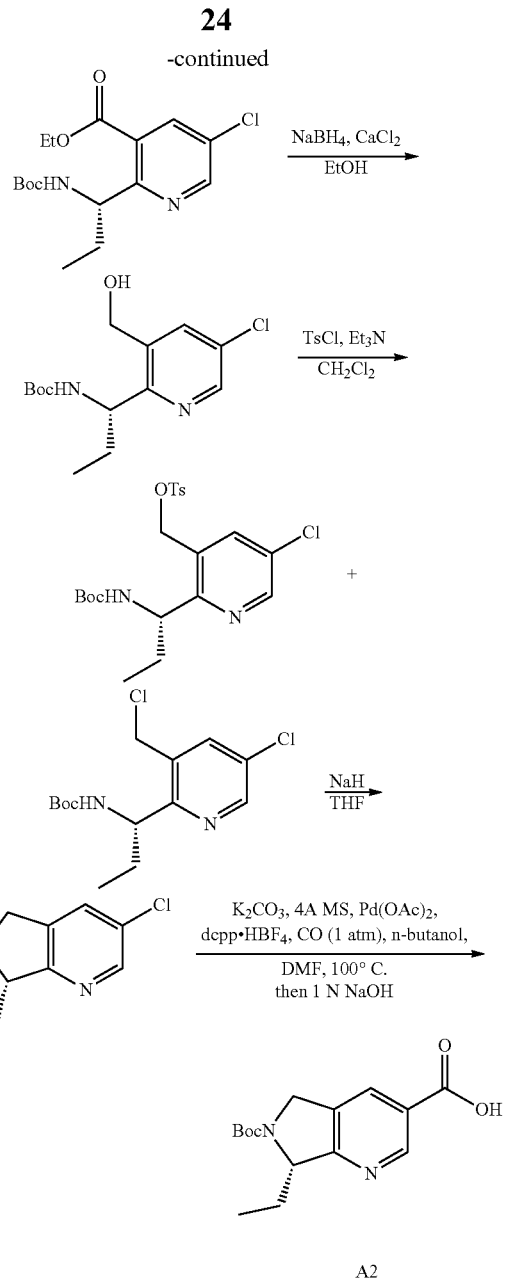

A2

Step 1: (S)-methyl 4-((tert-butoxycarbonyl)amino)-3-oxohexanoate

To a mixture of (S)-2-((tert-butoxycarbonyl)amino)butanoic acid (200 g, 0.985 mol) in THF (1 L) was added 1,1'-carbonyldiimidazole (176 g, 1.084 mol) at room temperature. The mixture was stirred at room temperature for 1 h. Then magnesium chloride (101 g, 1.084 mol) and potassium 3-methoxy-3-oxopropanoate (169 g, 1.084 mol) were added. After addition, the mixture was stirred at 50° C. for 3 h. TLC (petroleum ether:ethyl acetate=5:1) showed the starting material was consumed. The mixture was cooled and filtered; the filter cake was washed with THF (300 mL) and filtered. The combined filtrate was concentrated under reduced pressure and the residue was diluted with EtOAc (1 L) washed with water (800 mL), brine (800 mL), dried over anhydrous sodium sulfate, filtered and concentrated under reduced pressure to give (S)-methyl 4-((tert-butoxycarbonyl)amino)-3-oxohexanoate (117 g, 45%) as a yellow oil, which was used in the next step directly without further purification.

Step 2: (S)-methyl 2-(1-((tert-butoxycarbonyl) amino)propyl)-5-chloronicotinate

To a solution of (S)-methyl 4-((tert-butoxycarbonyl) amino)-3-oxohexanoate (117 g, 0.452 mol) in anhydrous THF (1.0 L) was added potassium tert-butoxide (51.3 g, 0.474 mol) in portions at 0° C. After stirring for 1 h at 0° C., 1,4-diazabicyclo[2.2.2]octane (53.1 g, 0.474 mol) and 2-chloro-1,3-bis(dimethylamino)trimethinium hexafluorophosphate (145 g, 0.474 mol) were added portionwise to the mixture at 0° C. The mixture was stirred at room temperature for 3 h and the solution turned red. Ammonium acetate (104 g, 1.355 mol) was added to the solution, and the resulting mixture was stirred at room temperature overnight. TLC (petroleum ether: ethyl acetate=5:1) showed no starting material remaining. The mixture was cooled and filtered; the filtrate was concentrated under reduced pressure and the residue was diluted with EtOAc (1.5 L) and washed with water (1 L), brine (1 L), dried over anhydrous sodium sulfate, filtered and concentrated under reduced pressure. The residue was purified by silica gel chromatography, eluting with petroleum ether:ethyl acetate=25:1-17:1 to give (S)-methyl 2-(1-((tert-butoxycarbonyl)amino)propyl)-5-chloronicotinate (53 g, 36%) as a yellow oil. LC-MS $t_R$=0.961 min in 5-95AB_1.5 min chromatography (Merck RP-18e 25-2 mm), MS (ESI) m/z 272.9 [M-55]$^+$. $^1$H NMR (CDCl$_3$, 400 MHz): δ 8.61 (d, J=2.4 Hz, 1H), 8.18 (d, J=2.4 Hz, 1H), 5.71-5.54 (m, 1H), 3.94 (s, 3H), 1.86-1.83 (m, 1H), 1.60-1.58 (m, 1H), 1.26 (s, 9H), 0.95 (t, J=7.2 Hz, 3H).

Step 3: (S)-tert-butyl (1-(5-chloro-3-(hydroxymethyl)pyridin-2-yl)propyl)carbamate To a solution of (S)-methyl 2-(1-((tert-butoxycarbonyl) amino)propyl)-5-chloronicotinate (60 g, 0.183 mol) in anhydrous ethanol (800 mL) was added sodium borohydride portionwise (14.0 g, 0.366 mol) at 0° C. slowly and stirred for about 20 min. To the resulting mixture was added calcium chloride (20.1 g, 0.183 mol) at 0° C. slowly in four portions. The mixture was stirred at 0° C. for 1.5 h. TLC (petroleum ether:ethyl acetate=5:1) showed no starting material remaining. The mixture was quenched with saturated aqueous NH$_4$Cl solution (50 mL) at 0° C. slowly and then stirred for 30 min. The mixture was concentrated to remove part of the ethanol, then extracted with ethyl acetate (3×1.0 L). The combined organic layers were washed with water (2×1.0 L) and saturated aqueous NaHCO$_3$ solution (500 mL), dried over anhydrous sodium sulfate, filtered and concentrated under reduced pressure to give (S)-tert-butyl (1-(5-chloro-3-(hydroxymethyl)pyridin-2-yl)propyl)carbamate (50 g, 91%) as a yellow solid, which was used directly for the next step without further purification. LC-MS $t_R$=0.703 min in 5-95AB_1.5 min chromatography (Merck RP-18e 25-2 mm), MS (ESI) m/z 244.9 [M-55]$^+$.

Step 4: (S)-tert-butyl (1-(5-chloro-3-(chloromethyl) pyridin-2-yl)propyl)carbamate & (S)-(2-(1-((tert-butoxycarbonyl)amino)propyl)-5-chloropyridin-3-yl) methyl 4-methylbenzenesulfonate To a solution of (S)-tert-butyl (1-(5-chloro-3-(hydroxymethyl)pyridin-2-yl)propyl)carbamate (50 g, 0.167 mol) in CH$_2$Cl$_2$ (500 mL) was added triethylamine (50.5 g, 0.499 mol) and p-toluenesulfonyl chloride (63 g, 0.333 mol) at 0° C. The mixture was stirred at room temperature for 1.5 h. TLC (petroleum ether:ethyl acetate=5:1) showed no starting material remaining. The mixture was diluted with CH$_2$Cl$_2$ (500 mL), washed with water (2×1.0 L) and brine (1 L), dried over anhydrous Na$_2$SO$_4$, filtered and concentrated under reduced pressure. The residue was purified by silica gel chromatography (eluting with petroleum ether:ethyl acetate=0 to 10:1) to give (S)-tert-butyl (1-(5-chloro-3-(chloromethyl)pyridin-2-yl)propyl)carbamate (11 g, 21%) as a red solid and (S)-(2-(1-((tert-butoxycarbonyl)amino) propyl)-5-chloropyridin-3-yl)methyl 4-methylbenzenesulfonate (23 g, 30%) as a yellow solid. LC-MS $t_R$=0.840 min in 5-95AB_1.5 min chromatography (Merck RP-18e 25-2 mm), MS (ESI) m/z 262.9 [M-55]$^+$.

Step 5: (S)-tert-butyl 3-chloro-7-ethyl-5H-pyrrolo[3,4-b]pyridine-6(7H)-carboxylate Procedure same as that for tert-butyl (S)-3-chloro-7-isopropyl-5,7-dihydro-6H-pyrrolo[3,4-b]pyridine-6-carboxylate with (S)-tert-butyl (1-(5-chloro-3-(chloromethyl) pyridin-2-yl)propyl)carbamate (11 g, 34.6 mmol) and (S)-(2-(1-((tert-butoxycarbonyl)amino)propyl)-5-chloropyridin-3-yl)methyl 4-methylbenzenesulfonate as the starting materials. $^1$H NMR (CDCl$_3$, 400 MHz): δ 8.45 (s, 1H), 7.56 (s, 0.6H), 7.50 (s, 0.4H), 5.30 (s, 0.4H), 4.94 (s, 0.6H), 4.77 (d, J=15.6 Hz, 0.6H), 4.70 (d, J=15.6 Hz, 0.4H), 4.55 (s, 0.6H), 4.51 (s, 0.4H), 2.26-2.14 (m, 1H), 2.04-1.96 (m, 1H), 1.51 (s, 9H), 0.67 (t, J=7.6 Hz, 3H).

Step 6: (S)-6-(tert-butoxycarbonyl)-7-ethyl-6,7-dihydro-5H-pyrrolo[3,4-b]pyridine-3-carboxylic acid Potassium carbonate (33.8 g, 24.5 mmol) and 4 Å molecular sieves (11.30 g) were placed in a 50 mL round-bottom flask which was then flame dried. Palladium (II) acetate (757 mg, 3.26 mmol) and 1,3-bis(dicyclohexylphosphonium)propane bis(tetrafluoroborate) (3.98 g, 6.52 mmol) were added to the flask, which was then sealed with a septum. (S)-tert-butyl 3-chloro-7-ethyl-5H-pyrrolo[3,4-b]pyridine-6(7H)-carboxylate (23 g, 81.5 mmol) was dissolved in DMF (250 mL) and added to the flask, followed by 1-butanol (60.4 g, 815 mmol). The flask was then evacuated and backfilled with CO four times. CO gas (from a gas bag, a volume of 30 L) was then bubbled into the flask, with heating to 100° C. overnight. LCMS showed no starting material remaining. The reaction was then cooled to room temperature and 6 g of NaOH in 100 ml water was added. After stirring for 1 h, LCMS showed a 100% conversion to the acid product. The mixture was acidified to pH=3-4 with 1 N HCl solution and extracted with ethyl acetate (3×1 L). The combined organic layers were washed with water (2×1 L) and brine (1 L), dried over anhydrous sodium sulfate, filtered and concentrated under reduced pressure. The residue was purified by silica gel chromatography (eluting with petroleum ether: ethyl acetate=20:1-1:1) to give the desired product (20 g, 84%, ee=28.24%), which was then purified by SFC separation to give (S)-6-(tert-butoxycarbonyl)-7-ethyl-6,7-dihydro-5H-pyrrolo[3,4-b]pyridine-3-carboxylic acid (9 g, ee=95.49%) as a yellow solid.

SFC Separation Method:

Instrument: Thar SFC 200; Column: AD 300 mm*50 mm, 10 μm; Mobile phase: A: Supercritical CO$_2$, B: IPA (0.1% NH$_3$H$_2$O), A:B=75:25 at 200 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm. LC-MS $t_R$=0.813 min in 5-95AB_1.5 min chromatography (Merck RP-18e 25-2 mm), MS (ESI) m/z 292.9 [M+H]$^+$. $^1$H NMR (CDCl$_3$, 400 MHz): δ 9.23 (s, 1H), 7.28 (s, 0.6H), 8.23 (s, 0.4H), 5.21 (s, 0.4H), 5.11 (s, 0.6H), 4.89 (d, J=16.0 Hz, 0.6H), 4.80 (d, J=15.6 Hz, 0.4H), 4.65 (s, 0.6H), 4.61 (s, 0.4H), 2.25-2.14 (m, 1H), 2.08-2.04 (m, 1H), 1.53 (s, 9H), 0.68 (t, J=7.6 Hz, 3H).

Isomer SFC 1215-186-P1A_1 $t_R$=6.71 in 15 min chromatography (Column: AD-H, Method Name: 5-40_2.5 ml.met, ee=95.49%).

Preparation B1: (R)-2-amino-2-(4-(ethylsulfonyl)phenyl)ethanol

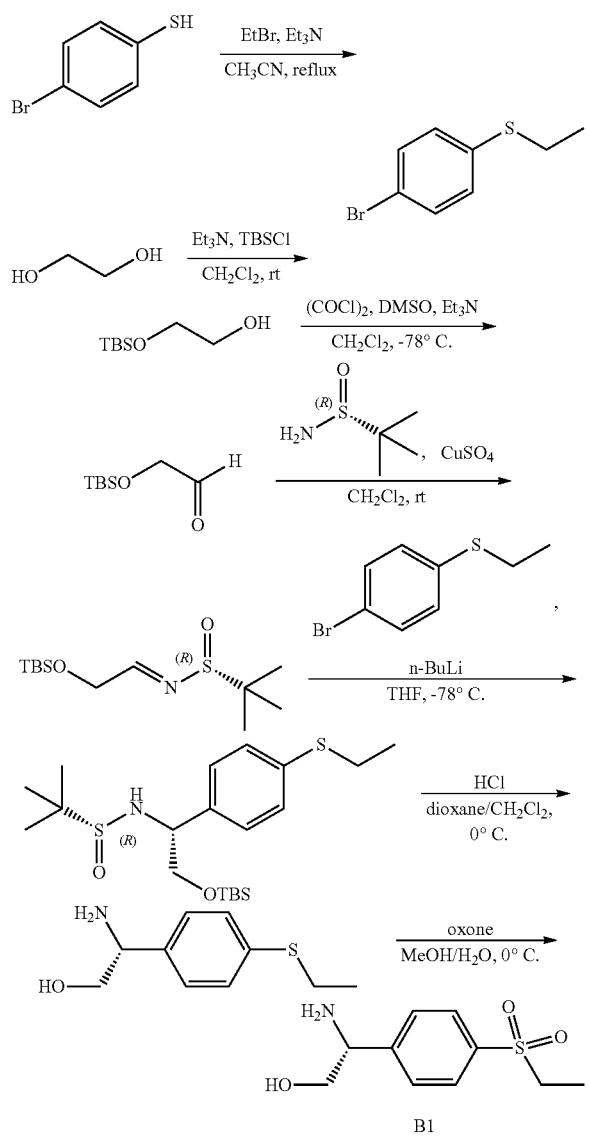

Step 1: (4-bromophenyl)(ethyl)sulfane

A mixture of 4-bromobenzenethiol (50 g, 0.26 mol), bromoethane (58 g, 0.53 mol) and triethylamine (78 g, 0.78 mol) in acetonitrile (1 L) was stirred at reflux for 17 h. The mixture was cooled to rt and filtered. The filtrate was concentrated under vacuum. The residue was purified by silica gel chromatography (eluting with petroleum ether) to give (4-bromophenyl)(ethyl)sulfane (55 g, 96%) as an oil. $^1$H NMR (CDCl$_3$, 400 MHz): δ 7.40-7.42 (dd, J=6.4, 2.0 Hz, 2H), 7.18-7.20 (dd, J=6.4, 2.0 Hz, 2H), 2.91-2.96 (q, J=7.2 Hz, 2H), 1.30-1.33 (t, J=7.2 Hz, 3H).

Step 2: 2-((tert-butyldimethylsilyl)oxy)ethanol

To a solution of ethane-1,2-diol (110 g, 1.77 mol) in anhydrous CH$_2$Cl$_2$ (1.1 L) was added triethylamine (215.2 g, 296 mL, 2.13 mol) at rt. The mixture was cooled to 0° C., then tert-butylchlorodimethylsilane (267.1 g, 1.77 mol) dissolved in CH$_2$Cl$_2$ (300 mL) was added dropwise over 1 h. The mixture was stirred at rt overnight. The reaction mixture was quenched with saturated aqueous NH$_4$Cl solution (400 mL) and separated. The aqueous phase was extracted with MTBE (2×400 mL). The combined organic layers were concentrated under vacuum and the residue was redissolved in MTBE (400 mL). The MTBE layer was washed with water (2×500 mL) and brine (500 mL), dried over anhydrous sodium sulfate, filtered and concentrated under vacuum to give 2-((tert-butyldimethylsilyl)oxy)ethanol (280 g, 90%) as a slight oil, which was used for the next step directly without further purification. $^1$H NMR (CDCl$_3$, 400 MHz): δ 3.64-3.66 (m, 2H), 3.57-3.60 (m, 2H), 0.85 (s, 9H), 0.02 (s, 6H).

Step 3: 2-((tert-butyldimethylsilyl)oxy)acetaldehyde

To a solution of CH$_2$Cl$_2$ (1.8 L) cooled to −30° C. was added oxalyl chloride (79.2 g, 52.8 mL, 624 mmol) dropwise. The mixture was cooled to −78° C., then DMSO (62.5 g, 88.5 mL, 1.25 mmol) was added dropwise. After addition, the mixture was stirred at −78° C. for 30 min. A solution of 2-((tert-butyldimethylsilyl)oxy)ethanol (100 g, 567 mmol) dissolved in CH$_2$Cl$_2$ (200 mL) was added slowly at −78° C. The reaction mixture was stirred at −78° C. for 1 h. Triethylamine (287 g, 395 mL, 2.84 mmol) was added dropwise at −78° C. The mixture was stirred at −78° C. for 30 min and then rt overnight. The reaction mixture was washed with water (1 L), 1 N HCl (2×1 L), saturated aqueous NaHCO$_3$ solution (1 L) and brine (1 L). The organic layer was dried over anhydrous sodium sulfate, filtered and concentrated under vacuum to give 2-((tert-butyldimethylsilyl)oxy)acetaldehyde (98.5 g, 99.8%) as a brown oil, which was used for the next step directly without further purification. $^1$H NMR (CDCl$_3$, 400 MHz): δ 9.70 (s, 1H), 4.22 (s, 2H), 0.93 (s, 9H), 0.11 (s, 6H).

Step 4: (R,E)-N-(2-((tert-butyldimethylsilyl)oxy)ethylidene)-2-methylpropane-2-sulfinamide A mixture of 2-((tert-butyldimethylsilyl)oxy)acetaldehyde (93.5 g, 0.54 mol), (R)-2-methylpropane-2-sulfinamide (78.8 g, 0.65 mol) and copper (II) sulfate (215 g, 1.35 mol) in anhydrous CH$_2$Cl$_2$ (1.5 L) was stirred at rt for 16 h. The mixture was quenched with H$_2$O (800 mL) and separated. The aqueous phase was extracted with CH$_2$Cl$_2$ (2×1 L). The combined organic layers were washed with water (1 L) and brine (1 L), dried over anhydrous sodium sulfate, filtered and concentrated under vacuum. The residue was purified by silica gel chromatography (eluting with petroleum ether:ethyl acetate=8:1) to give (R,E)-N-(2-((tert-butyldimethylsilyl)oxy)ethylidene)-2-methylpropane-2-sulfinamide (38.5 g, 26%) as a yellow oil. $^1$H NMR (CDCl$_3$, 400 MHz): δ 7.96-7.97 (t, J=3.2 Hz, 1H), 4.44-4.45 (d, J=2.8 Hz, 2H), 1.11 (s, 9H), 0.00 (s, 6H).

Step 5: (R)—N—((R)-2-((tert-butyldimethylsilyl)oxy)-1-(4-(ethylthio)phenyl)ethyl)-2-methylpropane-2-sulfinamide To a solution of (4-bromophenyl)(ethyl)sulfane (28.9 g, 133.1 mmol) in anhydrous THF (500 mL) was added dropwise n-butyllithium (73 mL, 181.5 mmol, 2.5 M in hexanes) at −78° C. The mixture was stirred at −78° C. for 30 min. A solution of (R,E)-N-(2-((tert-butyldimethylsilyl)oxy)ethylidene)-2-methylpropane-2-sulfinamide (33.5 g, 121 mmol) in anhydrous THF (100 mL) was added to the mixture at −78° C. The mixture was stirred at −78° C. for 2 h, then allowed to warm to rt and stirred for 2 h. The mixture was quenched with saturated aqueous NH$_4$Cl solution (200 mL) and extracted with ethyl acetate (3×300 mL). The combined organic layer was washed with water (200 mL) and brine (200 mL), dried over anhydrous Na$_2$SO$_4$, filtered and concentrated under vacuum. The residue was purified by silica gel chromatography (eluting with petroleum ether: ethyl acetate=15:1) three times to afford (R)—N—((R)-2-((tert-butyldimethylsilyl)oxy)-1-(4-(ethylthio)phenyl)ethyl)-2-methylpropane-2-sulfinamide (22 g, 44%) as a yellow oil. $^1$H NMR (CDCl$_3$, 400 MHz): δ 7.21-7.24 (d, J=7.2 Hz, 2H), 7.18-7.21 (d, J=8.4 Hz, 2H), 4.42-4.45 (dd, J=8.8, 2.4 Hz, 1H), 4.21 (brs, 1H), 3.69-3.73 (dd, J=10.4, 4.4 Hz, 1H), 3.51-3.56 (t, J=9.6 Hz, 1H), 2.87-2.92 (q, J=7.6 Hz, 2H), 1.25-1.29 (t, J=7.2 Hz, 3H), 1.18 (s, 9H), 0.88 (s, 9H), 0.02 (s, 6H). LCMS $t_R$=1.010 min in 5-95AB_1.5 min chromatography (MK RP18e 25-2 mm), MS (ESI) m/z 437.9 [M+Na]$^+$. Isomer SFC $t_R$=3.607 and 4.014 min in 12 min chromatography (AD-H_5_5_40_2.3 5 ML), ee=90.85%.

Step 6: (R)-2-amino-2-(4-(ethylthio)phenyl)ethanol

To a solution of (R)—N—((R)-2-((tert-butyldimethylsilyl)oxy)-1-(4-(ethylthio)phenyl)ethyl)-2-methylpropane-2-sulfinamide (22 g, 52.9 mmol) in CH$_2$Cl$_2$ (250 mL) was added HCl (26.5 mL, 4 N in dioxane) at 0° C. The mixture was stirred at rt for 2 h. LCMS showed no starting material remaining. The mixture was concentrated under reduced pressure to afford crude (R)-2-amino-2-(4-(ethylthio)phenyl)ethanol HCl salt (12.3 g, 100%) as a brown solid, which was used for the next step directly without further purification. LCMS $t_R$=1.226 min in 0-30AB_2 min chromatography (Xtimate 3 μm, C18, 2.1*30 mm), MS (ESI) m/z 180.9 [M-OH]$^+$.

Step 7: (R)-2-amino-2-(4-(ethylsulfonyl)phenyl)ethanol

To a mixture of (R)-2-amino-2-(4-(ethylthio)phenyl)ethanol (15.2 g, 65.0 mmol) in methanol (200 mL) was added dropwise a solution of oxone reagent (80.0 g, 130.0 mmol) in water (200 mL) at 0° C. The mixture was stirred at rt for 1.5 h; LCMS showed no starting material remaining. The mixture was filtered and methanol was removed under reduced pressure. The aqueous phase was extracted with EtOAc (2×80 mL), then the aqueous layer was basified to pH=8-9 with solid sodium carbonate portionwise at 0° C., then this solution was lyophilized (contained the Na$_2$CO$_3$). The solid was dissolved in CH$_2$Cl$_2$:MeOH (3:1, 600 mL) and stirred for 30 min, filtered, then concentrated under reduced pressure. The residue was purified by silica gel chromatography (eluting with CH$_2$Cl$_2$:MeOH=1:0 to 4:1) to give (R)-2-amino-2-(4-(ethylsulfonyl)phenyl)ethanol (11.5 g, 77%) as a white solid. LC-MS $t_R$=0.738 min in 0-30CD_ POS chromatography (Xtimate ODS 2.1*30 mm, 3 μm), MS (ESI) m/z 230.1 [M+H]$^+$. Isomer SFC $t_R$=6.99 min in 30 min chromatography (CD-PH_10-80_B_08 ML), ee=97.42%. $^1$H NMR (D$_2$O, 400 MHz): δ 7.82-7.84 (d, J=8.0 Hz, 2H), 7.54-7.56 (d, J=8.4 Hz, 2H), 4.33-4.35 (t, J=6.4 Hz, 1H), 3.72-3.78 (m, 2H), 3.19-3.25 (q, J=7.6 Hz, 2H), 1.03-1.07 (t, J=7.6 Hz, 3H).

Preparation B2: (R)-1-(4-(ethylsulfonyl)phenyl)-2-methoxyethan-1-amine

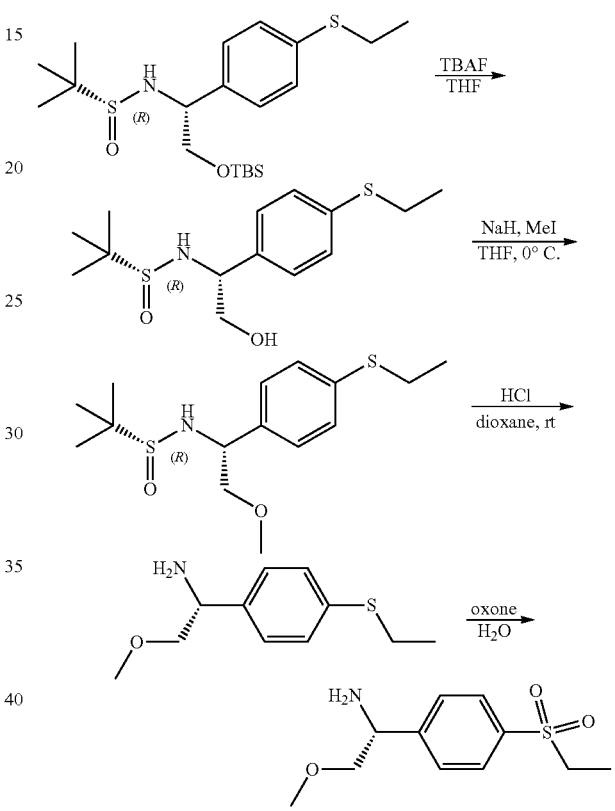

Step 1: (R)—N—((R)-1-(4-(ethylthio)phenyl)-2-hydroxyethyl)-2-methylpropane-2-sulfinamide To a solution of (R)—N—((R)-2-((tert-butyldimethylsilyl)oxy)-1-(4-(ethylthio)phenyl)ethyl)-2-methylpropane-2-sulfinamide (2.0 g, 4.8 mmol) in THF (30 mL) at rt was added TBAF (2.5 g, 9.6 mmol). The mixture was stirred at room temperature for 1 h. The mixture was washed with saturated aqueous NaHCO$_3$ solution (15 mL) and brine (15 mL), dried over anhydrous sodium sulfate, filtered and concentrated under reduced pressure. The residue was purified by silica gel chromatography (eluting with petroleum ether:ethyl acetate=1:1-1:3) to give (R)—N—((R)-1-(4-(ethylthio)phenyl)-2-hydroxyethyl)-2-methylpropane-2-sulfinamide (0.8 g, 80%) as a white solid. $^1$H NMR (DMSO-d$_6$, 400 MHz): δ 7.29-7.24 (m, 4H), 5.08 (t, J=6.0 Hz, 1H), 4.96 (d, J=4.0 Hz, 1H), 4.26-4.22 (m, 1H), 3.54 (t, J=6.4 Hz, 2H), 2.96 (q, J=7.2 Hz, 2H), 1.22 (t, J=7.2 Hz, 3H), 1.12 (s, 9H). LC-MS $t_R$=0.815 min in 5-95AB_1.5 min chromatography (Merck RP-18e 25-2 mm), MS (ESI) m/z 302.1 [M+H]$^+$.

Step 2: (R)—N—((R)-1-(4-(ethylthio)phenyl)-2-methoxyethyl)-2-methylpropane-2-sulfinamide To a solution of (R)—N—((R)-1-(4-(ethylthio)phenyl)-2-hydroxyethyl)-2-methylpropane-2-sulfinamide (450 mg, 1.50 mmol) in anhydrous THF (8 mL) was added sodium hydride (180 mg, 4.50 mmol, 60% in mineral oil) at 0° C. The mixture was stirred at 0° C. for 30 min. Iodomethane (320 mg, 2.25 mmol) was added and the mixture was stirred at room temperature overnight. The mixture was quenched with water (5 mL) and extracted with ethyl acetate (3×15 mL). The combined organic layers were dried over anhydrous $Na_2SO_4$, filtered and concentrated under reduced pressure. The residue was purified by silica gel chromatography eluting with petroleum ether/ethyl acetate 1/1 to afford (R)—N—((R)-1-(4-(ethylthio)phenyl)-2-methoxyethyl)-2-methylpropane-2-sulfinamide (250 mg, 53%) as a yellow oil. $^1$H NMR (DMSO-$d_6$, 400 MHz): δ 7.31-7.24 (m, 4H), 5.03 (d, J=5.2 Hz, 1H), 4.42-4.37 (m, 1H), 3.57-3.54 (m, 1H), 3.50-3.45 (m, 1H), 3.25 (s, 3H), 2.96 (q, J=7.2 Hz, 2H), 1.22 (t, J=7.2 Hz, 3H), 1.09 (s, 9H).

Step 3: (R)-1-(4-(ethylthio)phenyl)-2-methoxyethanamine

Procedure same as that for (S)—N—((S)-1-(4-(ethylsulfonyl)phenyl)-2-hydroxyethyl)-7-isopropyl-6,7-dihydro-5H-pyrrolo[3,4-b]pyridine-3-carboxamide with (R)—N—((R)-1-(4-(ethylthio)phenyl)-2-methoxyethyl)-2-methylpropane-2-sulfinamide as the starting material.

Step 4: (R)-1-(4-(ethylsulfonyl)phenyl)-2-methoxyethanamine

To a solution of (R)-1-(4-(ethylthio)phenyl)-2-methoxyethanamine (196 mg, 0.79 mmol, HCl salt) in water (15 mL) was added oxone (972 mg, 1.58 mmol) at room temperature. The mixture was stirred at room temperature for 2 h. The mixture was lyophilized directly. After lyophilization, the crude product was purified by silica gel chromatography eluting with $CH_2Cl_2$:MeOH=9:1 to give (R)-1-(4-(ethylsulfonyl)phenyl)-2-methoxyethanamine (170 mg, 77%, HCl salt) as a white solid. Isomer SFC $t_R$=4.463 min in 15 min chromatography (Column: OD-H; Method Name: OD-H_5_5_40_2,35 ML.M, ee=100%).

Preparation B3: (R)-2-ethoxy-1-(4-(ethylsulfonyl)phenyl)ethan-1-amine

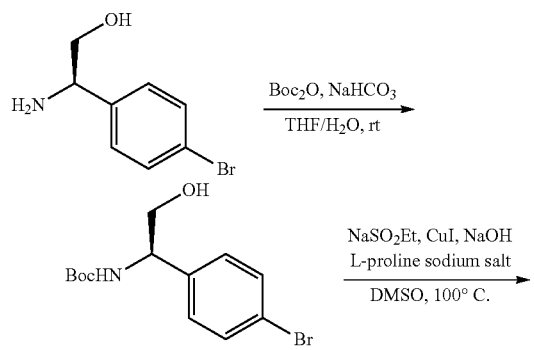

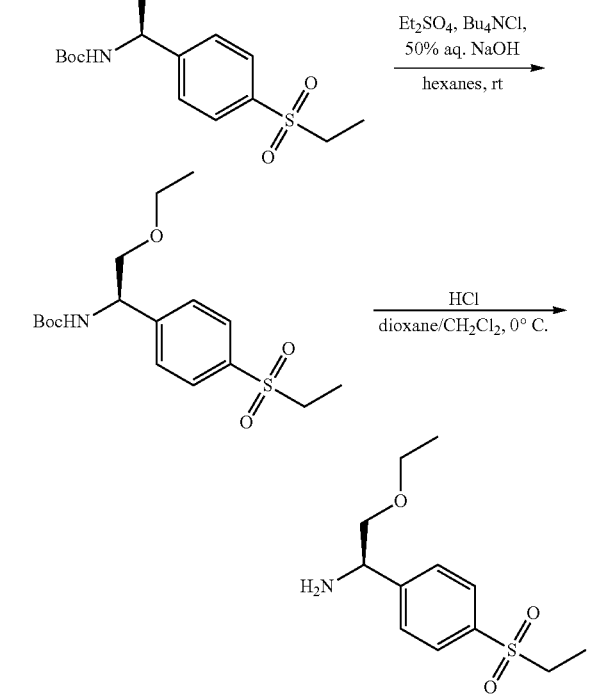

Step 1: tert-butyl (R)-(1-(4-bromophenyl)-2-hydroxyethyl)carbamate

To a mixture of (R)-2-amino-2-(4-bromophenyl)ethan-1-ol HCl salt (20.22 g, 80.4 mmol) in THF (200 mL) was added di-tert-butyl dicarbonate (18.4 g, 84.4 mmol) and saturated aqueous sodium bicarbonate (100 mL). The mixture was stirred for 3 h at rt. The mixture was diluted with EtOAc (200 mL). The organic layer was separated and washed with water (100 mL) and brine (50 mL), dried over $Na_2SO_4$, filtered and concentrated under reduced pressure. Crude tert-butyl (R)-(1-(4-bromophenyl)-2-hydroxyethyl)carbamate (25.03 g, 98.5% yield) was used without further purification. LC-MS $t_R$=1.38 min (2 min chromatography), m/z 260.0, 262.0 [M-55]$^+$.

Step 2: tert-butyl (R)-(1-(4-(ethylsulfonyl)phenyl)-2-hydroxyethyl)carbamate To a mixture of tert-butyl (R)-(1-(4-bromophenyl)-2-hydroxyethyl)carbamate (10.1 g, 31.9 mmol) in DMSO (100 mL) was added ethane sulfinic acid sodium salt (14.8 g, 128 mmol), copper (I) iodide (2.4 g, 12.8 mmol), L-proline sodium salt (1.8 g, 12.8 mmol) and 5% aqueous NaOH solution (2.56 mL, 3.19 mmol). The mixture was degassed with $N_2$ gas for 15 min. The mixture was then heated at 100° C. for 18 h. LC-MS showed the reaction to be complete. After cooling to rt, the mixture was diluted with EtOAc (200 mL) and water (200 mL). The organic layer was separated, washed with water (100 mL), saturated aqueous ammonium chloride solution (100 mL) and brine (50 mL), dried over $Na_2SO_4$, filtered and concentrated under reduced pressure. The residue was purified by silica gel chromatography (1:0 $CH_2Cl_2$:MeOH, gradient to 9:1) to afford 8.75 g tert-butyl (R)-(1-(4-(ethylsulfonyl)phenyl)-2-hydroxyethyl)carbamate (83% yield) as an off-white solid. LC-MS $t_R$=1.05 min (2 min chromatography), m/z 230.2 [M-99]⁺, 274.3 [M-55]⁺.

Step 3: tert-butyl (R)-(2-ethoxy-1-(4-(ethylsulfonyl) phenyl)ethyl)carbamate

To a mixture of tert-butyl (R)-(1-(4-(ethylsulfonyl)phenyl)-2-hydroxyethyl)carbamate (88.8 mg, 0.267 mmol), in hexanes (4 mL) and 50% aqueous NaOH solution (56 μL, 0.694 mmol) was added tetrabutylammonium chloride (1.5 mg, 4.01 μmol) and diethyl sulfate (52 μL, 0.401 mmol). The mixture was stirred for 6 h at rt. LCMS showed formation of the desired product, with some undissolved starting material still present. The mixture was diluted with EtOAc (15 mL) and water (15 mL). The organic layer was separated, washed with water (10 mL) and brine (10 mL), dried over $Na_2SO_4$, filtered, and concentrated under reduced pressure. The residue was purified by silica gel chromatography (0:1 EtOAc:hexanes, gradient to 2:3) to afford 49 mg tert-butyl (R)-(2-ethoxy-1-(4-(ethylsulfonyl)phenyl)ethyl) carbamate (51% yield) as a clear oil.

Step 4: (R)-2-ethoxy-1-(4-(ethylsulfonyl)phenyl) ethan-1-amine

A solution of tert-butyl (R)-(2-ethoxy-1-(4-(ethylsulfonyl)phenyl)ethyl)carbamate (49 mg, 0.137 mmol) in HCl (2 mL, 4 N in dioxane) was stirred at room temperature for 2 h. The mixture was concentrated under reduced pressure to afford crude (R)-2-ethoxy-1-(4-(ethylsulfonyl)phenyl) ethan-1-amine as a yellow oil, which was used for the next step directly without further purification.

Preparation B4: methyl (R)-2-(2-amino-2-(4-(ethylsulfonyl)phenyl)ethoxy)acetate

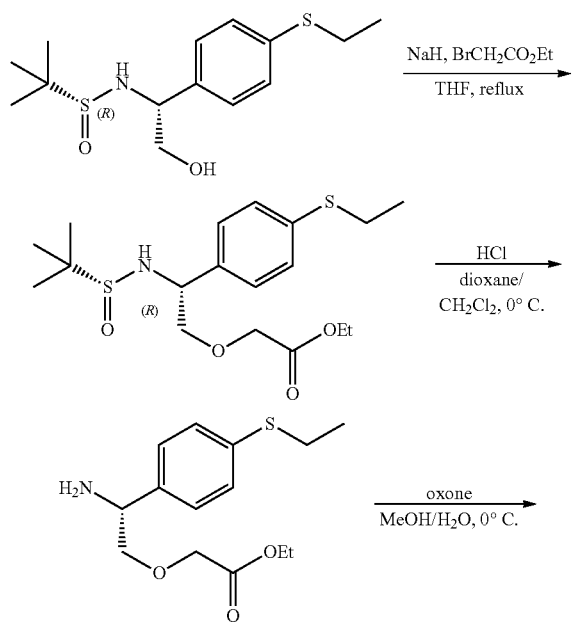

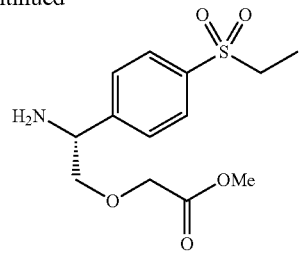

Step 1: (R)—N—((R)-1-(4-(ethylthio)phenyl)-2-hydroxyethyl)-2-methylpropane-2-sulfinamide To a solution of (R)—N—((R)-2-((tert-butyldimethylsilyl)oxy)-1-(4-(ethylthio)phenyl)ethyl)-2-methylpropane-2-sulfinamide (2.0 g, 4.8 mmol) in THF (30 mL) at rt was added TBAF (2.5 g, 9.6 mmol). The mixture was stirred at room temperature for 1 h. The mixture was washed with saturated aqueous $NaHCO_3$ solution (15 mL) and brine (15 mL), dried over anhydrous sodium sulfate, filtered and concentrated under reduced pressure. The residue was purified by silica gel chromatography (eluting with petroleum ether:ethyl acetate=1:1-1:3) to give (R)—N—((R)-1-(4-(ethylthio)phenyl)-2-hydroxyethyl)-2-methylpropane-2-sulfinamide (0.8 g, 80%) as a white solid. $^1$H NMR (DMSO-$d_6$, 400 MHz): δ 7.29-7.24 (m, 4H), 5.08 (t, J=6.0 Hz, 1H), 4.96 (d, J=4.0 Hz, 1H), 4.26-4.22 (m, 1H), 3.54 (t, J=6.4 Hz, 2H), 2.96 (q, J=7.2 Hz, 2H), 1.22 (t, J=7.2 Hz, 3H), 1.12 (s, 9H). LC-MS $t_R$=0.815 min in 5-95AB_1.5 min chromatography (Merck RP-18e 25-2 mm), MS (ESI) m/z 302.1 [M+H]⁺.

Step 2: ethyl 2-((R)-2-((R)-1,1-dimethylethylsulfinamido)-2-(4-(ethylthio)phenyl)ethoxy)acetate To a solution of (R)—N—((R)-1-(4-(ethylthio)phenyl)-2-hydroxyethyl)-2-methylpropane-2-sulfinamide (100 mg, 0.33 mmol) and ethyl 2-bromoacetate (110 mg, 0.66 mmol) in THF (3 mL) at 0° C. was added sodium hydride (40 mg, 1 mmol, 60% in mineral oil). The mixture was heated to reflux and stirred for 16 h. The mixture was cooled to rt and quenched with saturated aqueous $NH_4Cl$ solution (5 mL) and extracted with ethyl acetate (3×5 mL). The combined organic layer was washed with water (3×5 mL), brine (5 mL), dried over anhydrous sodium sulfate, filtered and concentrated under reduced pressure. The residue was purified by silica gel chromatography (eluting with petroleum ether:ethyl acetate=1:2) to give ethyl 2-((R)-2-((R)-1,1-dimethylethylsulfinamido)-2-(4-(ethylthio)phenyl)ethoxy)acetate (80 mg, 64%) as an colorless oil. LC-MS $t_R$=1.084 min in 10-80AB_2 MIN min chromatography (Xtimate ODS 2.1*30 mm, 3 μm), MS (ESI) m/z 388.2 [M+H]⁺.

Step 3: (R)-ethyl 2-(2-amino-2-(4-(ethylthio)phenyl) ethoxy)acetate

Procedure same as that for (R)-2-ethoxy-1-(4-(ethylsulfonyl)phenyl)ethan-1-amine, with ethyl 2-((R)-2-((R)-1,1-dimethylethylsulfinamido)-2-(4-(ethylthio)phenyl)ethoxy) acetate as the starting material.

Step 4: (R)-methyl 2-(2-amino-2-(4-(ethylsulfonyl) phenyl)ethoxy)acetate HCl salt Procedure same as that for (R)-1-(4-(ethylsulfonyl)phenyl)-2-methoxyethanamine, using (R)-ethyl 2-(2-amino-2-

(4-(ethylthio)phenyl)ethoxy)acetate (180 mg, 0.56 mmol) as a starting material. LC-MS $t_R$=0.120 min in 0-30AB_2 min chromatography (Xtimate, 2.1*30 mm, 3 μm), MS (ESI) m/z 302.1 [M+I-1]$^+$. HCl preparative HPLC method Mobile phase A: water with 0.05% HCl; Mobile phase B: $CH_3CN$; Flow rate: 30 mL/min. Detection: UV 220 nm/254 nm; Column: Synergi Max-RP 150*30 mm*4 μm; Column temperature: 30° C. Time in min, % A, % B=0.00, 99, 1; 8.00, 75, 25; 8.20, 0, 100; 10.00, 0, 100.

Preparation B5: (R)-2-amino-2-(5-(ethylsulfonyl) pyridin-2-yl)ethanol

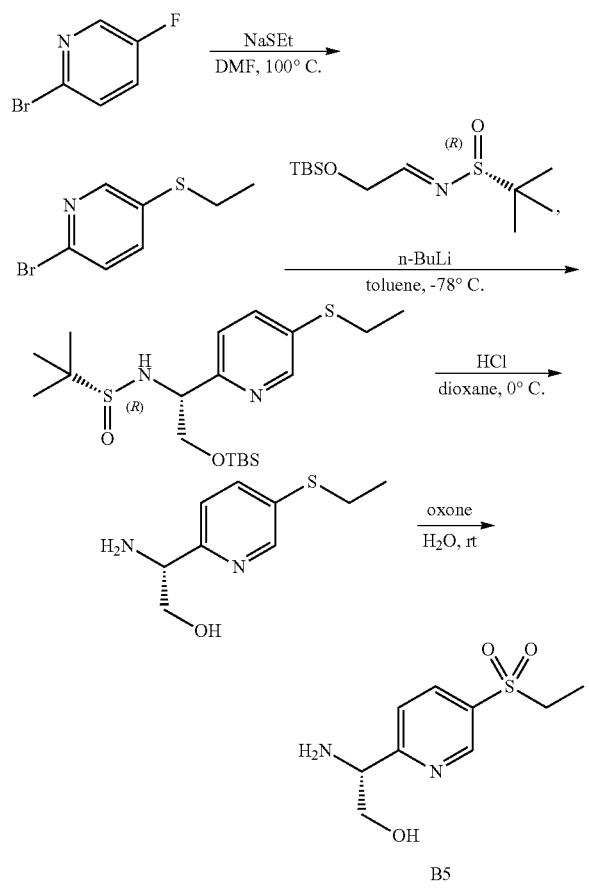

Step 1: 2-bromo-5-(ethylthio)pyridine

To a mixture of 2-bromo-5-fluoropyridine (6.28 g, 35.66 mmol) in anhydrous DMF (60 mL) was added sodium ethanethiolate (3 g, 35.66 mmol). The mixture was stirred at 100° C. for 3 h. TLC (petroleum ether/ethyl acetate 10/1) showed that the starting material was not consumed completely. Additional sodium ethanethiolate (0.9 g, 9.56 mmol) was added to the mixture. The mixture was stirred at 100° C. for 12 h. The mixture was quenched with $H_2O$ (150 mL) and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 80/1) to afford 2-bromo-5-(ethylthio)pyridine (7.0 g, 90%) as a colorless oil. LC-MS $t_R$=0.717 min in 5-95AB_1.5 min chromatography (Welch Merck RP-18e 25-2 mm), MS (ESI) m/z 217.6 [M+H]$^+$.

Step 2: (R)—N—((R)-2-((tert-butyldimethylsilyl) oxy)-1-(5-(ethylthio)pyridin-2-yl)ethyl)-2-methyl-propane-2-sulfinamide To a solution of toluene (60 mL) was added n-BuLi (10.6 mL, 26.48 mmol, 2.5 M in hexanes) dropwise at −78° C.; the internal temperature did not exceed −50° C. A solution of 2-bromo-5-(ethylthio)pyridine (3.85 g, 17.65 mmol) in toluene (10 mL) was then added to the reaction mixture at −78° C.; the internal temperature did not exceed −65° C. The mixture was stirred at −78° C. for 1 h. A solution of (R,E)-N-(2-((tert-butyldimethylsilyl)oxy)ethylidene)-2-methylpropane-2-sulfinamide (4.90 g, 17.65 mmol) in toluene (10 mL) was added to the reaction mixture at −78° C.; the internal temperature did not exceed −60° C. The mixture was stirred at −78° C. for another 2 h. The mixture was quenched with brine (150 mL) at −78° C. and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 10/1 to 3/1) to afford (R)—N—((R)-2-((tert-butyldimethylsilyl)oxy)-1-(5-(ethylthio)pyridin-2-yl)ethyl)-2-methylpropane-2-sulfinamide (3.0 g, 41%) as a pale yellow oil. LC-MS $t_R$=1.014 min in 5-95AB_1.5 min chromatography (Welch Merck RP-18e 25-2 mm), MS (ESI) m/z 417.2 [M+H]$^+$.

Step 3: (R)-2-amino-2-(5-(ethylthio)pyridin-2-yl) ethanol

Procedure same as that for (R)-2-amino-2-(4-(ethylthio) phenyl)ethanol with (R)—N—((R)-2-((tert-butyldimethylsilyl)oxy)-1-(5-(ethylthio)pyridin-2-yl)ethyl)-2-methylpropane-2-sulfinamide as the starting material.

Step 4: (R)-2-amino-2-(5-(ethylsulfonyl)pyridin-2-yl)ethanol

Procedure same as that for (R)-1-(4-(ethylsulfonyl)phenyl)-2-methoxyethanamine with (R)-2-amino-2-(5-(ethylthio)pyridin-2-yl)ethanol as the starting material.
$^1$H NMR (CD$_3$OD, 400 MHz): δ 9.08 (s, 1H), 8.35 (dd, J=2.0, 8.4 Hz, 1H), 7.79 (d, J=8.4 Hz, 1H), 4.70 (t, J=5.6 Hz, 1H), 4.03 (dd, J=4.8, 12.0 Hz, 1H), 3.91 (dd, J=4.8, 11.6 Hz, 1H), 3.29 (q, J=7.2 Hz, 2H), 1.25 (t, J=7.2 Hz, 3H).

Preparation C1: trans-4-(trifluoromethyl)cyclohexanecarbaldehyde

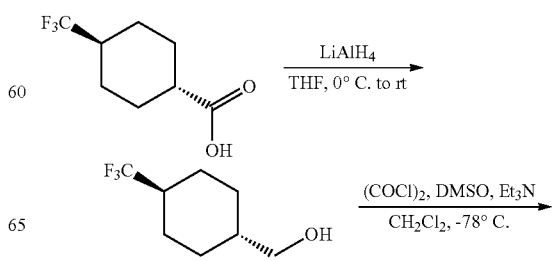

-continued

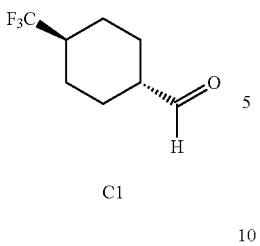

C1

Step 1: (trans-4-(trifluoromethyl)cyclohexyl)methanol

To a mixture of lithium aluminum hydride (11.6 g, 0.306 mol) in anhydrous THF (350 mL) was added a solution of trans-4-(trifluoromethyl)cyclohexanecarboxylic acid (30 g, 0.153 mol) in anhydrous THF (50 mL) at 0° C. dropwise. The mixture was stirred at 0° C. for 2 h. TLC (petroleum ether:ethyl acetate=10:1) showed no starting material remaining. The mixture was quenched with water (12 mL), 15% aqueous NaOH solution (24 mL) and H$_2$O (12 mL) successively. The mixture was filtered and the filtrate was concentrated under vacuum to give (trans-4-(trifluoromethyl)cyclohexyl)methanol (24 g, 86%) as a liquid. $^1$H NMR (CDCl$_3$, 400 MHz): δ 3.49-3.50 (d, J=6.0 Hz, 2H), 1.91-2.07 (m, 4H), 1.50-1.57 (m, 1H), 1.32-1.36 (m, 2H), 0.98-1.05 (m, 2H).

Step 2: trans-4-(trifluoromethyl)cyclohexanecarbaldehyde

To a mixture of oxalyl chloride (24.96 g, 13.84 mL, 197.7 mmol) in CH$_2$Cl$_2$ (250 mL) was added dropwise DMSO (20.72 g, 28 mL, 395.4 mmol) at −65° C. The mixture was stirred at −65° C. for 30 min. (trans-4-(trifluoromethyl)cyclohexyl)methanol (12 g, 65.9 mmol) dissolved in CH$_2$Cl$_2$ (50 mL) was added dropwise at −65° C. and the mixture was stirred at −65° C. for another 30 min. Triethylamine (66.4 g, 91.2 mL, 659 mmol) was added dropwise below −65° C. The mixture was stirred at −65° C. for 30 min, then stirred at room temperature for 1.5 h. The mixture was quenched with water (200 mL) and separated. The aqueous layer was extracted with CH$_2$Cl$_2$ (2×300 mL). The combined organic layers were washed with water (200 mL) and brine (200 mL), dried over anhydrous sodium sulfate, filtered and concentrated under vacuum. The residue was purified by silica gel chromatography (eluting with petroleum ether:ethyl acetate=10:1) to give trans-4-(trifluoromethyl)cyclohexanecarbaldehyde (8.9 g, 75%) as a slight yellow oil. $^1$H NMR (CDCl$_3$, 400 MHz): δ 9.70 (s, 1H), 2.16-2.65 (m, 3H), 2.04-2.12 (m, 3H), 1.00-1.39 (m, 4H).

Preparation C2: 6-(trifluoromethyl)tetrahydro-2H-pyran-3-carbaldehyde

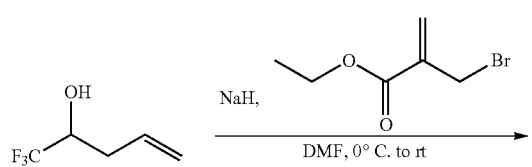

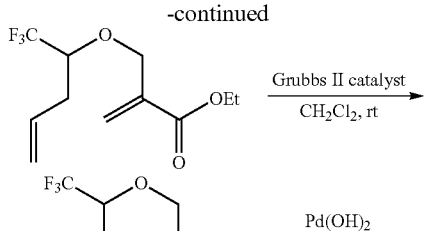

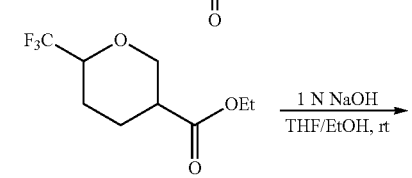

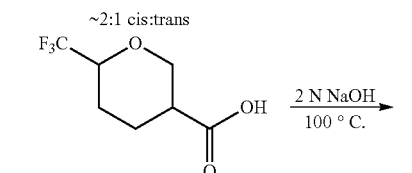

~2:1 cis:trans

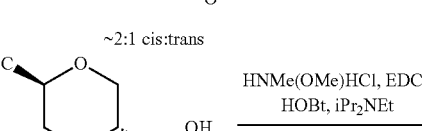

~2:1 cis:trans

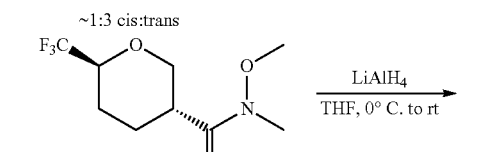

~1:3 cis:trans

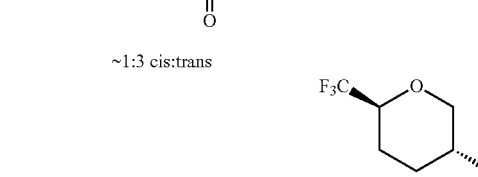

~1:3 cis:trans

C2

Step 1: ethyl 2-(((1,1,1-trifluoropent-4-en-2-yl)oxy)methyl)acrylate

To a solution of 1,1,1-trifluoropent-4-en-2-ol (6.7 g, 48 mmol) in anhydrous (dried with CaH$_2$) DMF (85 mL) was added sodium hydride (2.3 g, 57 mmol, 60% in mineral oil) in portions at 0° C. The mixture was stirred at 0° C. for 30 min, then ethyl 2-(bromomethyl)acrylate (9.2 g, 48 mmol) was added dropwise to the resulting mixture via syringe at 0° C. After addition, the mixture was stirred at room temperature for 2 h. TLC analysis (eluting with petroleum ether:ethyl acetate=10:1) showed that the starting material was consumed. The reaction was quenched with water (50 mL) at 0° C. and the aqueous layer was extracted with ethyl acetate (3×50 mL). The combined organic layers were washed successively with water (3×50 mL) and brine (50 mL), dried over anhydrous sodium sulfate, filtered and concentrated under reduced pressure. The crude residue was purified by silica gel chromatography (eluting with petroleum ether/ethyl acetate:gradient from 100/1 to 50/1) to afford ethyl 2-(((1,1,1-trifluoropent-4-en-2-yl)oxy)methyl) acrylate (6.6 g, 55%) as a pale yellow oil. $^1$H NMR (CDCl$_3$ 400 MHz): δ 6.31 (s, 1H), 5.89 (s, 1H), 5.85-5.74 (m, 1H), 5.23-5.07 (m, 2H), 4.52-4.43 (m, 1H), 4.38-4.15 (m, 3H), 3.82-3.68 (m, 1H), 2.50-2.35 (m, 2H), 1.38-1.20 (m, 3H).

Step 2: ethyl 6-(trifluoromethyl)-5,6-dihydro-2H-pyran-3-carboxylate

To a solution of ethyl 2-(((1,1,1-trifluoropent-4-en-2-yl)oxy)methyl)acrylate (6.6 g, 26.2 mmol) in anhydrous CH$_2$Cl$_2$ (2.6 L) was added Grubbs II catalyst (2.2 g, 2.62 mmol) under N$_2$. The mixture was stirred at room temperature for 3 h. TLC analysis (eluting with petroleum ether: ethyl acetate=10:1) showed that the reaction was complete. Water (2 L) was added to the mixture to quench the reaction. After partition, the organic layer was washed successively with water (3×2 L) then brine (2 L), dried over anhydrous sodium sulfate, filtered and concentrated under reduced pressure. The residue was purified by silica gel chromatography (eluting with petroleum ether/ethyl acetate:gradient from 100/1 to 80/1) to afford ethyl 6-(trifluoromethyl)-5,6-dihydro-2H-pyran-3-carboxylate (4.83 g, 82%) as a pale yellow oil. $^1$H NMR (CDCl$_3$ 400 MHz): δ 7.01 (d, J=2.8 Hz, 1H), 4.63-4.58 (m, 1H), 4.40-4.33 (m, 1H), 4.20 (q, J=7.2 Hz, 2H), 3.95-3.84 (m, 1H), 2.57-2.46 (m, 1H), 2.41-2.32 (m, 1H), 1.28 (t, J=7.2 Hz, 3H).

Step 3: ethyl 6-(trifluoromethyl)tetrahydro-2H-pyran-3-carboxylate

To a solution of ethyl 6-(trifluoromethyl)-5,6-dihydro-2H-pyran-3-carboxylate (4.83 g, 22 mmol) in anhydrous THF (130 mL) was added dry Pd(OH)$_2$ on carbon (2.7 g, 10% w/w). The mixture was stirred at room temperature for 16 h under H$_2$ (30 psi). TLC analysis (eluting with petroleum ether/ethyl acetate=10/1) showed that most of the starting material was not consumed. The mixture was filtered, then the filtrate was concentrated under reduced pressure and dissolved into anhydrous THF (60 mL). Dry Pd(OH)$_2$ on carbon (2.7 g, 10% w/w) was added to the mixture. The mixture was stirred at room temperature for 28 h under H$_2$ (30 psi). TLC analysis (eluting with petroleum ether/ethyl acetate=10/1) showed that the starting material was consumed. The mixture was filtered and the filtrate was concentrated under reduced pressure to afford crude ethyl 6-(trifluoromethyl)tetrahydro-2H-pyran-3-carboxylate (3.4 g, 70%) as a colorless oil, which was used for the next step directly without further purification. $^1$H NMR (CDCl$_3$ 400 MHz): δ 4.50 (d, J=11.6 Hz, 1H), 4.18 (q, J=7.2 Hz, 2H), 3.80-3.68 (m, 1H), 3.66 (d, J=3.2, 11.6 Hz, 1H), 2.55-2.49 (m, 1H), 2.43-2.35 (m, 1H), 1.95-1.81 (m, 1H), 1.75-1.65 (m, 2H), 1.25 (t, J=7.2 Hz, 3H).

Step 4: 6-(trifluoromethyl)tetrahydro-2H-pyran-3-carboxylic acid

To a solution of crude ethyl 6-(trifluoromethyl)tetrahydro-2H-pyran-3-carboxylate (2.0 g, 8.8 mmol) in THF (24 mL), EtOH (12 mL) was added 1 N aqueous NaOH solution (12 mL). The mixture was stirred at room temperature for 3 h. TLC analysis (eluting with petroleum ether:ethyl acetate=10:1) showed that the reaction was complete. The mixture was added to water (20 mL) and concentrated under reduced pressure to remove the organic solvent. The residue was washed with MTBE (20 mL) and adjusted to pH=4-5 with 1 N HCl solution. Then, the aqueous layer was extracted with EtOAc (3×20 mL). The combined organic layers were washed with brine (20 mL), dried over anhydrous sodium sulfate, filtered and concentrated under reduced pressure to afford crude 6-(trifluoromethyl)tetrahydro-2H-pyran-3-carboxylic acid (1.72 g, 98%) as a pale yellow oil, which was used for the next step directly without further purification. The ratio of cis:trans isomers was ~2:1 based on $^1$H NMR and $^{19}$F NMR analysis. $^1$H NMR (CDCl$_3$ 400 MHz): δ 8.56 (br s, 1H), 4.47 (d, J=12.0 Hz, 0.68H), 4.25 (d, J=12.0 Hz, 0.32H), 3.76-3.62 (m, 1.68H), 3.47 (t, J=11.2 Hz, 0.32H), 2.71-2.61 (m, 0.32H), 2.58-2.51 (m, 0.68H), 2.38-2.22 (m, 1H), 1.88-1.80 (m, 1H), 1.75-1.60 (m, 2H).

Step 5: 6-(trifluoromethyl)tetrahydro-2H-pyran-3-carboxylic acid

To a solution of crude 6-(trifluoromethyl)tetrahydro-2H-pyran-3-carboxylic acid (1.72 g, 8.69 mmol) was added a 2 N aqueous NaOH solution (76 mL). The mixture was stirred in sealed tube at 100° C. for 84 h. The mixture was diluted with water (20 mL) and washed with MTBE (50 mL). The aqueous layer was adjusted to pH=4-5 with 1 N HCl solution and extracted with EtOAc (3×50 mL). The combined organic layers were washed with brine (50 mL), dried over anhydrous sodium sulfate, filtered and concentrated under reduced pressure to afford crude 6-(trifluoromethyl)tetrahydro-2H-pyran-3-carboxylic acid (1.60 g, 93%) as a pale yellow oil, which was used for the next step directly without further purification. The ratio of cis:trans was ~1:3 based on $^1$H NMR and $^{19}$F NMR analysis. $^1$H NMR (CDCl$_3$ 400 MHz): δ 4.54 (d, J=12.0 Hz, 0.25H), 4.32 (dd, J=2.8, 11.6 Hz, 0.75H), 3.83-3.68 (m, 1.25H), 3.52 (t, J=11.2 Hz, 0.75H), 2.75-2.58 (m, 1H), 2.45-2.30 (m, 1H), 1.95-1.85 (m, 1H), 1.83-1.63 (m, 2H).

Step 6: N-methoxy-N-methyl-6-(trifluoromethyl)tetrahydro-2H-pyran-3-carboxamide To a solution of crude 6-(trifluoromethyl)tetrahydro-2H-pyran-3-carboxylic acid (1.0 g, 5.01 mmol) (~1:3 cis:trans ratio of isomers) in anhydrous CH$_2$Cl$_2$ (60 mL) was added N,O-dimethylhydroxylamine hydrochloride (980 mg, 10.10 mmol), EDCI (1.93 g, 10.10 mmol), HOBt (1.36 g, 10.10 mmol), and diisopropylethylamine (1.95 g, 15.15 mmol). The mixture was stirred at room temperature for 16 h. The mixture was diluted with water (60 mL) and extracted with CH$_2$Cl$_2$ (3×60 mL). The combined organic layers were washed with brine (60 mL), dried over anhydrous sodium sulfate, filtered and concentrated under reduced pressure. The residue was purified by silica gel chromatography (eluting with petroleum ether/ethyl acetate:gradient from 30/1 to 15/1) to afford N-methoxy-N-methyl-6-(trifluoromethyl)tetrahydro-2H-pyran-3-carboxamide (1.05 g, 87%) as a pale yellow oil. Note: The ratio of cis:trans was ~1:3 based on $^1$H NMR and $^{19}$F NMR analysis. $^1$H NMR (CDCl$_3$ 400 MHz): δ 4.30-4.24 (m, 0.25H), 4.22-4.15 (m, 0.75H), 3.90-3.68 (m, 4H), 3.62-3.52 (m, 1H), 3.24-3.14 (m, 2H), 3.10-2.98 (m, 1H), 2.14-2.04 (m, 1H), 1.95-1.80 (m, 2H), 1.80-1.65 (m, 2H).

Step 7: 6-(trifluoromethyl)tetrahydro-2H-pyran-3-carbaldehyde

To a solution of N-methoxy-N-methyl-6-(trifluoromethyl)tetrahydro-2H-pyran-3-carboxamide (90 mg, 0.373 mmol) (~1:3 cis:trans ratio of isomers) in anhydrous THF (5 mL) was added lithium aluminum hydride (0.75 mL, 0.746 mmol, 1 M in THF) dropwise at 0° C. under $N_2$. The mixture was stirred at 0° C. for 1 h. TLC analysis (eluting with petroleum ether/ethyl acetate: 5/1) showed that the reaction was complete. The mixture was quenched with saturated aqueous sodium sulfate solution (1 mL) and filtered. The filtrate was diluted with $CH_2Cl_2$ (60 mL) and washed with water (60 mL), 10% aqueous HCl solution (0.5 M, 60 mL), saturated aqueous $NaHCO_3$ solution (60 mL) and water (60 mL). The organic layer was dried over anhydrous sodium sulfate, filtered and concentrated under reduced pressure to afford crude 6-(trifluoromethyl)tetrahydro-2H-pyran-3-carbaldehyde (60 mg, 88%) as a pale yellow oil, which was used for the next step directly without further purification. The ratio of cis:trans was ~1:3 based on $^1H$ NMR and $^{19}F$ NMR analysis.

Preparation of Compounds of Formula I

Compounds of Formula (I) were prepared according to the general procedures outlined below.

Example 1

(S)-7-ethyl-N—((R)-1-(4-(ethylsulfonyl)phenyl)-2-methoxyethyl)-6-((trans-4-(trifluoromethyl)cyclohexyl)methyl)-6,7-dihydro-5H-pyrrolo[3,4-b]pyridine-3-carboxamide (1)

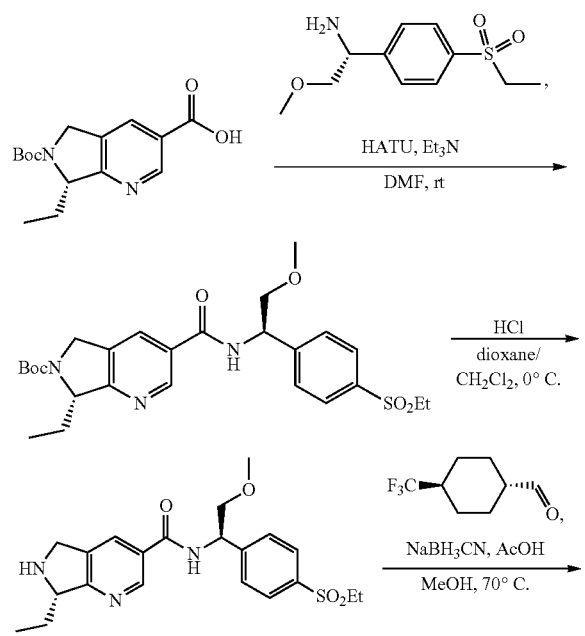

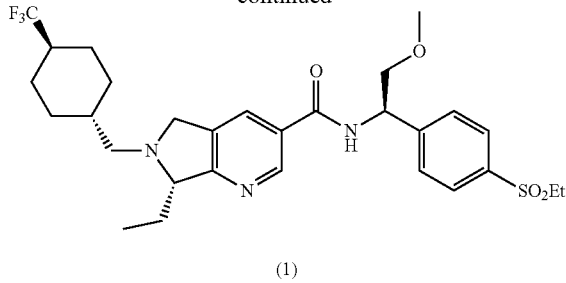

(1)

Step 1: (S)-tert-butyl 7-ethyl-3-(((R)-1-(4-(ethylsulfonyl)phenyl)-2-methoxyethyl)carbamoyl)-5H-pyrrolo[3,4-b]pyridine-6(7H)-carboxylate A mixture of (S)-6-(tert-butoxycarbonyl)-7-ethyl-6,7-dihydro-5H-pyrrolo[3,4-b]pyridine-3-carboxylic acid (1.40 g, 4.79 mmol), HATU (2.19 g, 5.75 mmol) and triethylamine (2.00 mL, 14.4 mmol) in DMF (25 mL) was stirred at rt for 30 min. (R)-1-(4-(ethylsulfonyl)phenyl)-2-methoxyethan-1-amine (1.28 g, 5.27 mmol) dissolved in DMF (5 mL) was added dropwise to the mixture at 0° C. The mixture was stirred at room temperature for 2 h. LCMS showed no starting material remaining. The reaction mixture was diluted with water (25 mL) and extracted with ethyl acetate (3×75 mL). The combined organic layers were washed with water (3×50 mL) and brine (50 mL), dried over anhydrous $Na_2SO_4$, filtered and concentrated under reduced pressure. The residue was purified by silica gel column chromatography (eluting with petroleum ether:ethyl acetate=1:6 to 1:8) to give (S)-tert-butyl 7-ethyl-3-(((R)-1-(4-(ethylsulfonyl)phenyl)-2-methoxyethyl)carbamoyl)-5H-pyrrolo[3,4-b]pyridine-6(7H)-carboxylate (2.40 g, 97%) as a yellow solid.

Step 2: (S)-7-ethyl-N—((R)-1-(4-(ethylsulfonyl)phenyl)-2-hydroxyethyl)-6,7-dihydro-5H-pyrrolo[3,4-b]pyridine-3-carboxamide To a solution of (S)-tert-butyl 7-ethyl-3-(((R)-1-(4-(ethylsulfonyl)phenyl)-2-methoxyethyl)carbamoyl)-5H-pyrrolo[3,4-b]pyridine-6(7H)-carboxylate (2.40 g, 4.63 mmol) in $CH_2Cl_2$ (25 mL) was added dropwise HCl (7 mL, 4 N in dioxane) at 0° C. The mixture was stirred at room temperature for 2 h. TLC (petroleum ether:ethyl acetate=1:3) showed no starting material remaining. The mixture was concentrated under reduced pressure. The residue was basified to pH=9-10 with 10% aqueous NaOH solution, then extracted with ethyl acetate (5×200 mL). The combined organic layers were dried over anhydrous sodium sulfate, filtered and concentrated under reduced pressure to afford (S)-7-ethyl-N—((R)-1-(4-(ethylsulfonyl)phenyl)-2-methoxyethyl)-6,7-dihydro-5H-pyrrolo[3,4-b]pyridine-3-carboxamide (1.93 g, 100%) as a yellow-red solid, which was used for the next step directly without further purification.

Step 3: (S)-7-ethyl-N—((R)-1-(4-(ethylsulfonyl)phenyl)-2-methoxyethyl)-6-((trans-4-(trifluoromethyl)cyclohexyl)methyl)-6,7-dihydro-5H-pyrrolo[3,4-b]pyridine-3-carboxamide To a mixture of (S)-7-ethyl-N—((R)-1-(4-(ethylsulfonyl)phenyl)-2-hydroxyethyl)-6,7-dihydro-5H-pyrrolo[3,4-b]pyridine-3-carboxamide (1.93 g, 4.63 mmol) and trans-4-

(trifluoromethyl)cyclohexanecarbaldehyde (1.25 g, 6.95 mmol) in anhydrous MeOH (25 mL) was added acetic acid dropwise until the pH was between 6 and 7. Sodium cyanoborohydride (1.16 g, 18.5 mmol) was added portionwise at rt. The mixture was heated to 70° C. and stirred for 1 h. The mixture was cooled to rt and quenched with saturated aqueous sodium bicarbonate (50 mL), then extracted with ethyl acetate (2×75 mL). The combined organic layers were dried over anhydrous $Na_2SO_4$, filtered and concentrated under reduced pressure. The residue was purified by silica gel chromatography (eluting with ethyl acetate), then purified further by SFC separation (AD-H) and acidic (HCl) preparative HPLC to give (S)-7-ethyl-N—((R)-1-(4-(ethylsulfonyl)phenyl)-2-methoxyethyl)-6-((trans-4-(trifluoromethyl)cyclohexyl)methyl)-6,7-dihydro-5H-pyrrolo[3,4-b]pyridine-3-carboxamide (867 mg, HCl salt, 30%) as a light yellow solid. LC-MS $t_R$=0.696 min in 5-95AB_1.5 min chromatography (RP-18e 25-2 mm), MS (ESI) m/z 582.2 [M+H]$^+$. $^1$H NMR (CD$_3$OD, 400 MHz): δ 9.05 (d, J=1.6 Hz, 1H), 8.27 (s, 1H), 7.90 (d, J=8.4 Hz, 2H), 7.71 (d, J=8.4 Hz, 2H), 5.43 (dd, J=5.2 Hz, 8.4 Hz, 1H), 5.10 (d, J=14.8 Hz, 1H), 4.86-4.81 (m, 1H), 4.70 (d, J=14.8 Hz, 1H), 3.84-3.73 (m, 2H), 3.51-3.38 (m, 2H), 3.41 (s, 3H), 3.21 (q, J=7.2 Hz, 2H), 2.29-1.91 (m, 8H), 1.51-1.39 (m, 4H), 1.34 (t, J=7.2 Hz, 3H), 1.21 (t, J=7.2 Hz, 3H). $^{19}$F NMR (CD$_3$OD, 400 MHz): δ −75.38. SFC separation condition: Instrument: Thar 80; Column: AD 250 mm*50 mm, 10 μm; Mobile phase: A: Supercritical CO$_2$, B: i-PrOH (0.05% NH$_3$H$_2$O), A:B=60:40 at 200 mL/min; Column Temp: 38° C. Nozzle Pressure: 100 Bar; Nozzle Temp: 60° C.; Evaporator Temp: 20° C.; Trimmer Temp: 25° C.; Wavelength: 220 nm. HCl preparative HPLC method Mobile phase A: water with 0.05% HCl; Mobile phase B: CH$_3$CN; Flow rate: 90 mL/min; Detection: UV 220 nm/254 nm; Column: Phenomenex luna C18 250*50 mm*10 μm; Column temperature: 30° C. Time in min, % A, % B=0.00, 90, 10; 50.00, 40, 60; 50.20, 0,100; 55.00, 0, 100;

Example 2

(R)-2-((S)-7-ethyl-6-((trans-4-(trifluoromethyl)cyclohexyl)methyl)-6,7-dihydro-5H-pyrrolo[3,4-b]pyridine-3-carboxamido)-2-(4-(ethylsulfonyl)phenyl)ethyl carbamate (2)

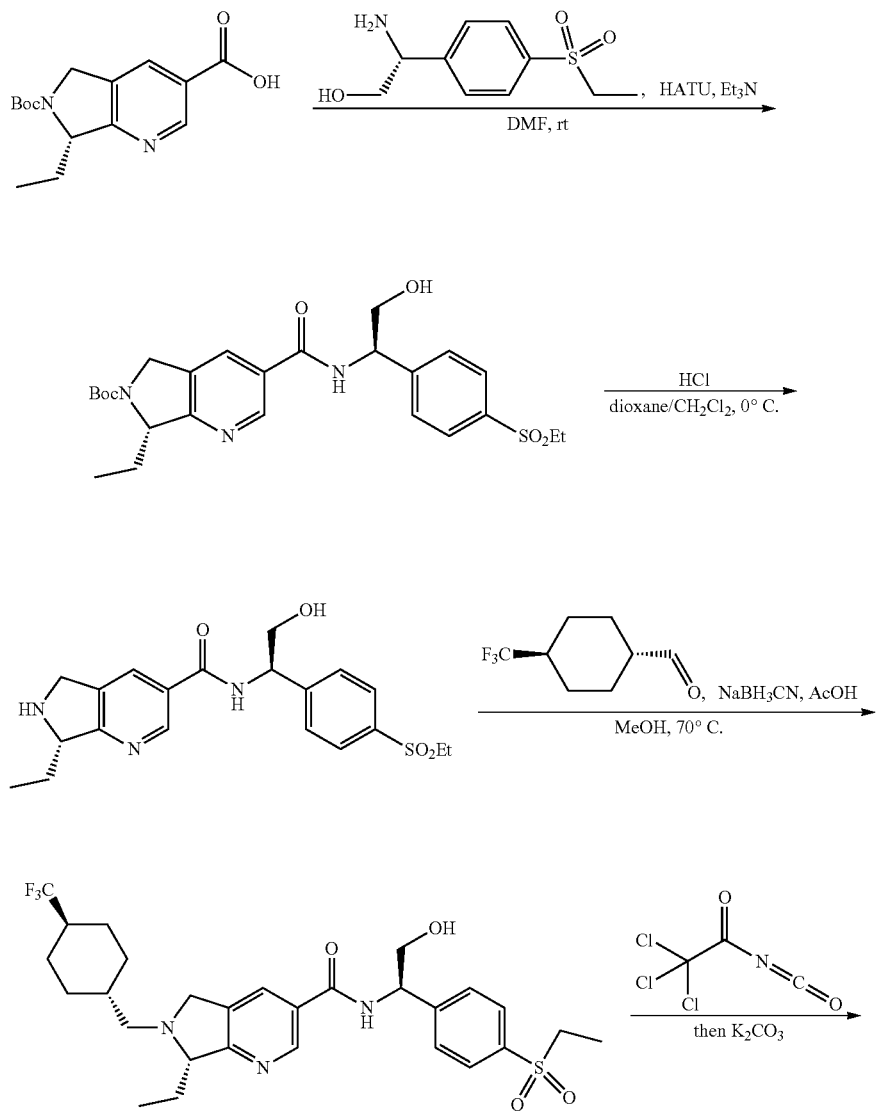

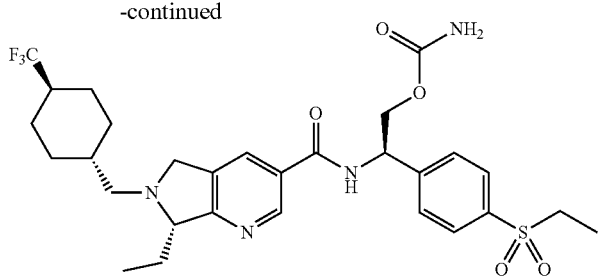

(2)

Step 1: (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate A mixture of (S)-6-(tert-butoxycarbonyl)-7-ethyl-6,7-dihydro-5H-pyrrolo[3,4-b]pyridine-3-carboxylic acid (8 g, 27.4 mmol), HATU (12.5 g, 32.9 mmol) and triethylamine (8.32 g, 11.5 mL, 82.2 mmol) in DMF (120 mL) was stirred at rt for 0.5 h. (R)-2-amino-2-(4-(ethylsulfonyl)phenyl)ethanol (6.9 g, 30.1 mmol) dissolved in DMF (30 mL) was added dropwise to the mixture at 0° C. The mixture was stirred at rt for 2 h. LCMS showed no starting material remaining. The reaction mixture was diluted with water (100 mL) and extracted with ethyl acetate (3×200 mL). The combined organic layers were washed with water (3×100 mL) and brine (100 mL), dried over anhydrous $Na_2SO_4$, filtered and concentrated under reduced pressure. The residue was purified by silica gel column chromatography (eluting with petroleum ether:ethyl acetate=1:6 to 1:8) to give (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate (9.0 g, 65%) as a yellow solid. $^1H$ NMR ($CDCl_3$, 400 MHz): δ 8.96 (s, 1H), 8.01 (s, 1H), 7.88-7.90 (d, J=8.0 Hz, 2H), 7.60-7.62 (d, J=8.4 Hz, 2H), 7.29-7.30 (m, 1H), 5.32-5.35 (m, 1H), 5.04-5.13 (m, 1H), 4.76-4.82 (m, 1H), 4.55-4.59 (m, 1H), 4.00-4.13 (m, 2H), 3.08-3.13 (q, J=7.6 Hz, 2H), 2.19-2.22 (m, 2H), 1.53 (s, 9H), 1.28-1.30 (q, J=7.6 Hz, 3H), 0.65-0.68 (q, J=7.2 Hz, 3H). LC-MS $t_R$=0.702 min in 5-95AB_1.5 min chromatography (MERCK RP-18e 25-2 mm), MS (ESI) m/z 504.0 [M+H]$^+$.

Step 2: (S)-7-ethyl-N—((R)-1-(4-(ethylsulfonyl)phenyl)-2-hydroxyethyl)-6,7-dihydro-5H-pyrrolo[3,4-b]pyridine-3-carboxamide To a solution of (S)-tert-butyl 7-ethyl-3-(((R)-1-(4-(ethylsulfonyl)phenyl)-2-hydroxyethyl)carbamoyl)-5H-pyrrolo[3,4-b]pyridine-6(7H)-carboxylate (9.0 g, 17.9 mmol) in $CH_2Cl_2$ (100 mL) was added dropwise HCl (30 mL, 4 N in dioxane) at 0° C. The mixture was stirred at rt for 2 h. TLC (petroleum ether:ethyl acetate=1:3) showed no starting material remaining. The mixture was concentrated under reduced pressure. The residue was basified to pH=9-10 with 10% aqueous NaOH solution, then extracted with ethyl acetate (5×200 mL). The combined organic layers were dried over anhydrous sodium sulfate, filtered and concentrated under reduced pressure to afford (S)-7-ethyl-N—((R)-1-(4-(ethylsulfonyl)phenyl)-2-hydroxyethyl)-6,7-dihydro-5H-pyrrolo[3,4-b]pyridine-3-carboxamide (7.2 g, 100%) as a yellow-red solid, which was used for the next step directly without further purification.

Step 3: (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide To a mixture of (S)-7-ethyl-N—((R)-1-(4-(ethylsulfonyl)phenyl)-2-hydroxyethyl)-6,7-dihydro-5H-pyrrolo[3,4-b]pyridine-3-carboxamide (7.2 g, 17.8 mmol) and trans-4-(trifluoromethyl)cyclohexanecarbaldehyde (4.81 g, 26.7 mmol) in anhydrous MeOH (100 mL) was added acetic acid dropwise until the pH was between 6 and 7. Sodium cyanoborohydride (4.47 g, 71.2 mmol) was added portionwise at rt. The mixture was heated to 70° C. and stirred for 1 h. The mixture was cooled to rt and quenched with saturated aqueous sodium bicarbonate (150 mL), then extracted with ethyl acetate (2×150 mL). The combined organic layers were dried over anhydrous $Na_2SO_4$, filtered and concentrated under reduced pressure. The residue was purified by silica gel chromatography (eluting with ethyl acetate), then purified further by SFC separation (AD-H) and acidic (HCl) preparative HPLC to give (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide (total 4.5 g, HCl salt, 46%) as a light yellow solid. LC-MS $t_R$=0.662 min in 5-95AB_1.5 min chromatography (RP-18e 25-2 mm), MS (ESI) m/z 568.0 [M+H]$^+$. $^1H$ NMR ($CD_3OD$, 400 MHz): δ 9.07 (s, 1H), 8.27 (s, 1H), 7.88-7.90 (d, J=8.0 Hz, 2H), 7.67-7.69 (d, J=8.0 Hz, 2H), 5.26-5.29 (t, J=6.0 Hz, 1H), 5.06-5.10 (m, 2H), 4.70-4.80 (m, 1H), 3.90-3.91 (d, J=6.4 Hz, 2H), 3.30-3.43 (m, 2H), 3.16-3.21 (q, J=7.2 Hz, 2H), 1.97-2.22 (m, 8H), 1.18-1.46 (m, 10H). $^{19}F$ NMR ($CD_3OD$, 400 MHz): δ −75.39. HCl preparative HPLC method Mobile phase A: water with 0.05% HCl; Mobile phase B: $CH_3CN$; Flow rate: 80 mL/min. Detection: UV 220 nm/254 nm. Column: Phenomenex Gemini C18 250*50 mm*5um. Column temperature: 30° C. Time in min: % A:% B; 0.00:70:30; 8.00:45:55; 8.20:0:100; 10.00:0:100.

Step 4: (R)-2-((S)-7-ethyl-6-((trans-4-(trifluoromethyl)cyclohexyl)methyl)-6,7-dihydro-5H-pyrrolo[3,4-b]pyridine-3-carboxamido)-2-(4-(ethylsulfonyl)phenyl)ethyl carbamate To a solution of (S)-7-ethyl-N—((R)-1-(4-(ethylsulfonyl)phenyl)-2-hydroxyethyl)-6-((trans-4-(trifluoromethyl)cyclohexyl)methyl)-6,7-dihydro-5H-pyrrolo[3,4-b]pyridine-3-carboxamide ($t_R$=5.52 min on AD-H) (20 mg, HCl salt, 0.035 mmol) in anhydrous $CH_2Cl_2$ (2 mL) at 0° C. was added trichloromethyl isocyanate (11.3 mg, 0.07 mmol). The mixture was stirred at room temperature for 30 min. The mixture was quenched with MeOH (1 mL) and concentrated under reduced pressure. The residue was then redissolved in MeOH (2 mL), to which potassium carbonate (5 mg, 0.035 mmol) was added and the mixture was stirred at room temperature for 2 h. The mixture was concentrated under reduced pressure and the residue was purified by HCl preparative HPLC separation to give (R)-2-((S)-7-ethyl-6-((trans-4-(trifluoromethyl)cyclohexyl)methyl)-6,7-dihydro-5H-pyrrolo[3,4-b]pyridine-3-carboxamido)-2-(4-(ethylsulfonyl)phenyl)ethyl carbamate (4.50 mg, HCl salt, 20%) as a white solid. LC-MS $t_R$=0.657 min in 5-95AB_1.5 min chromatography (Merck RP-18e 25-2 mm), MS (ESI) m/z 611.1 [M+H]$^+$. $^1$H NMR (CD$_3$OD, 400 MHz): δ 9.05 (s, 1H), 8.23 (s, 1H), 7.91 (d, J=8.4 Hz, 2H), 7.71 (d, J=8.4 Hz, 2H), 5.50 (t, J=6.4 Hz, 1H), 5.03-5.02 (m, 1H), 4.77-4.68 (m, 2H), 4.40 (d, J=6.4 Hz, 2H), 3.42-3.36 (m, 2H), 3.21 (q, J=7.6 Hz, 2H), 2.20-1.92 (m, 8H), 1.45-1.21 (m, 7H), 1.20 (t, J=7.6 Hz, 3H). $^{19}$F NMR (CD$_3$OD, 400 MHz): δ −74.88 ppm. Isomer SFC: $t_R$=2.202 min in 3 min chromatography (Column: AD-H_3 UM_5_5_40_4 ML), ee=96.80%. HCl preparative HPLC method. Mobile phase A: water with 0.05% HCl; Mobile phase B: CH$_3$CN; Flow rate: 30 mL/min; Detection: UV 220 nm/254 nm; Column: Synergi Max-RP 150*30 mm*4 μm. Column temperature: 30° C. Time in min, % A, % B=0.00, 77, 23; 8.00, 67, 33; 8.20, 0, 100; 10.00, 0, 100.

The following compounds in Table 1 were prepared according to the methods described herein. Where designated, an "*" indicates that although a single diastereomer was isolated, the absolute configuration about these positions was not fully characterized, however the relative stereochemistry at one of the designated positions to the other designated position is as shown. Accordingly, groups (pairs) of compounds exist (e.g., compounds 3 and 4; and 5 and 6) where a single diastereomer was isolated and tested, but where the absolute stereochemistry about the "*" is arbitrarily defined. For example in compound 3, the trifluoromethyl group is trans relative to its connection to the dihydropyrrolopyridine core.

TABLE 1

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 3 | (structure shown) | 0.637 (1.5 min) 584.1 [M + H]$^+$ | 9.07 (d, J = 1.6 Hz, 1H), 8.29 (s, 1H), 7.92 (d, J = 8.4 Hz, 2H), 7.72 (d, J = 8.0 Hz, 2H), 5.43-5.47 (m, 1H), 5.09-5.15 (m, 1H), 4.73-4.84 (m, 3H), 4.23 (d, J = 11.2 Hz, 1H), 3.76-3.92 (m, 3H), 3.33-3.40 (m, 2H), 3.42 (s, 3H), 3.22 (q, J = 7.2 Hz, 2H), 2.15-2.36 (m, 4H), 1.93-1.96 (m, 1H), 1.70-1.74 (m, 1H), 1.50-1.55 (m, 1H), 1.30-1.36 (m, 3H), 1.24 (t, J = 7.6 Hz, 3H). | −80.58 | A2, B2, C2 |
| 4 | (structure shown) | 0.636 (1.5 min) 584.0 [M + H]$^+$ | 9.07 (d, J = 1.6 Hz, 1H), 8.29 (s, 1H), 7.92 (d, J = 8.4 Hz, 2H), 7.72 (d, J = 8.0 Hz, 2H), 5.43-5.47 (m, 1H), 5.09-5.15 (m, 1H), 4.73-4.84 (m, 3H), 4.23 (d, J = 11.2 Hz, 1H), 3.76-3.92 (m, 3H), 3.33-3.40 (m, 2H), 3.42 (s, 3H), 3.22 (q, J = 7.2 Hz, 2H), 2.15-2.36 (m, 4H), 1.93-1.96 (m, 1H), 1.70-1.74 (m, 1H), 1.50-1.55 (m, 1H), 1.30-1.36 (m, 3H), 1.24 (t, J = 7.6 Hz, 3H). | −80.57 | A2, B2, C2 |
| 5 | (structure shown) | 0.635 (1.5 min) 584.1 [M + H]$^+$ | 9.08 (s, 1H), 8.28 (s, 1H), 7.92 (d, J = 8.4 Hz, 2H), 7.72 (d, J = 8.4 Hz, 2H), 5.43-5.47 (m, 1H), 5.10-5.13 (m, 1H), 4.73-4.83 (m, 2H), 3.89-4.14 (m, 2H), 3.76-3.89 (m, 5H), 3.42 (s, 3H), 3.22 (q, J = 7.2 Hz, 2H), 2.26-2.32 (m, 4H), 1.98-2.11 (m, 1H), 1.70-1.86 (m, 1H), 1.30-1.35 (m, 3H), 1.23 (t, J = 7.2 Hz, 3H). | −80.72 | A2, B2, C2 |

TABLE 1-continued

| Cpd. No. | Structure | LC/MS (tR, method, m/z) | ¹H NMR (CD₃OD) | ¹⁹F NMR (CD₃OD) | Intermediate Components |
|---|---|---|---|---|---|
| 6 | 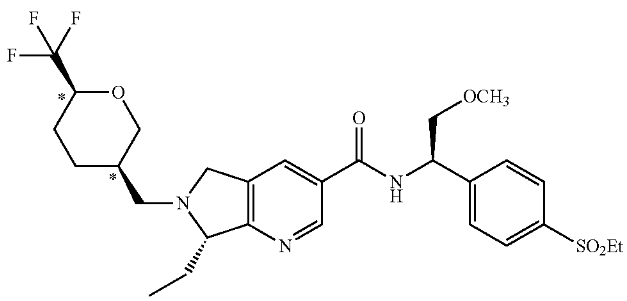 | 0.636 (1.5 min) 584.1 [M + H]⁺ | 9.08 (s, 1H), 8.29 (s, 1H), 7.92 (d, J = 8.0 Hz, 2H), 7.72 (d, J = 8.4 Hz, 2H), 5.43-5.47 (m, 1H), 5.10-5.13 (m, 1H), 4.74-4.82 (m, 2H), 4.10-4.14 (m, 2H), 3.76-3.89 (m, 5H), 3.42 (s, 3H), 3.22 (q, J = 7.2 Hz, 2H), 2.25-2.32 (m, 4H), 1.98-2.10 (m, 1H), 1.71-1.86 (m, 1H), 1.30-1.35 (m, 3H), 1.23 (t, J = 7.2 Hz, 3H). | −80.61 | A2, B2, C2 |
| 7 | 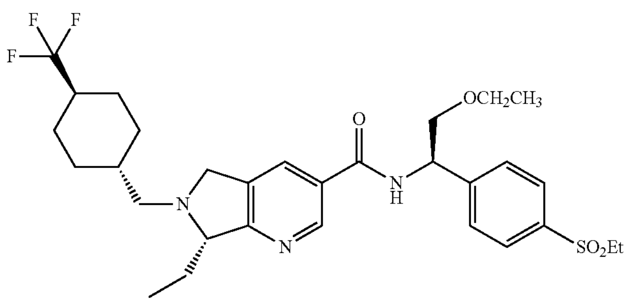 | 1.20 (2 min) 610.7 [M + H]⁺ | 9.25 (s, 1H), 9.13 (s, 1H), 8.30 (s, 1H), 7.95 (d, J = 7.6 Hz, 2H), 7.76 (d, J = 7.6 Hz, 2H), 5.46 (m, 1H), 5.10 (m, 1H), 4.86 (m, 2H), 3.87 (m, 2H), 3.64 (q, J = 7.2 Hz, 2H), 3.37 (m, 1H), 3.25 (q, J = 7.6 Hz, 2H), 2.57 (m, 1H), 2.21 (m, 1H), 2.07 (m, 1H), 2.15-1.92 (m, 6H), 1.83 (m, 1H), 1.48 (m, 2H), 1.35 (t, J = 6.8 Hz, 3H), 1.26 (t, J = 7.6 Hz, 3H), 1.25 (d, J = 6.8 Hz, 6H). | −75.4 | A1, B3, C1 |
| 8 | 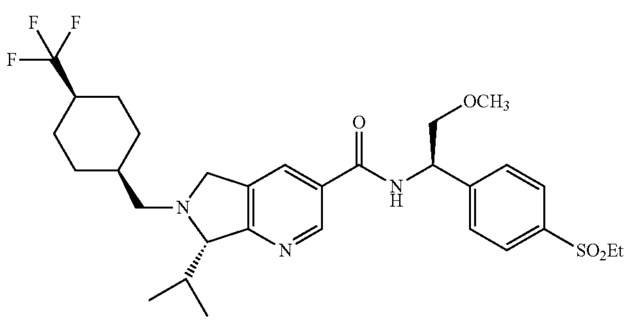 | 0.659 (1.5 min) 596.1 [M + H]⁺ | 9.24 (d, J = 7.6 Hz, 1H), 9.08 (s, 1H), 8.26 (s, 1H), 7.90 (d, J = 8.8 Hz, 2H), 7.71 (d, J = 8.4 Hz, 2H), 5.45-5.43 (m, 1H), 5.15-5.05 (m, 1H), 4.75-4.65 (m, 1H), 3.82-3.75 (m, 2H), 3.55-3.45 (m, 2H), 3.41 (s, 3H), 3.21 (q, J = 7.6 Hz, 2H), 2.55-2.45 (m, 1H), 2.35-2.25 (m, 2H), 1.81-1.65 (m, 9H), 1.30 (d, J = 6.8 Hz, 3H), 1.21 (t, J = 7.2 Hz, 3H), 1.08 (d, J = 6.4 Hz, 3H). | | A1, B2, C1 |
| 9 | 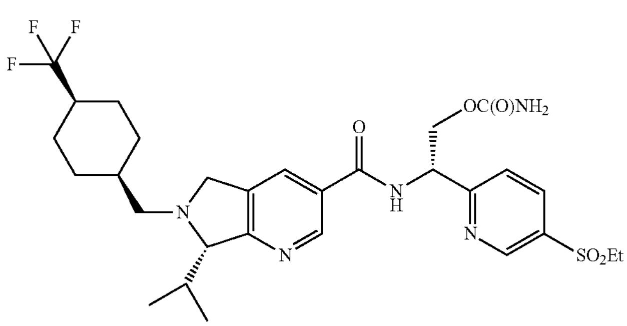 | 0.630 (1.5 min) 626.1 [M + H]⁺ | 9.35-9.30 (m, 0.4H), 9.11 (s, 1H), 9.04 (d, J = 1.6 Hz, 1H), 8.30 (dd, J = 2.0, 8.0 Hz, 1H), 8.27 (s, 1H), 7.77 (d, J = 8.4 Hz, 1H), 5.61 (t, J = 6.0 Hz, 1H), 5.14-5.09 (m, 3H), 4.57-4.52 (m, 2H), 3.50 (q, J = 4.0 Hz, 2H), 3.28 (t, J = 6.8 Hz, 2H), 2.54-2.51 (m, 1H), 2.32-2.29 (m, 2H), 1.84-1.76 (m, 6H), 1.70-1.66 (m, 2H), 1.31 (d, J = 6.8 Hz, 3H), 1.26 (q, J = 7.6 Hz, 3H), 1.08 (d, J = 4.0 Hz, 3H) | | A1, B5, C1 Carbamate formation performed by the procedure described in Example 2, Step 4. |

TABLE 1-continued

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 10 | 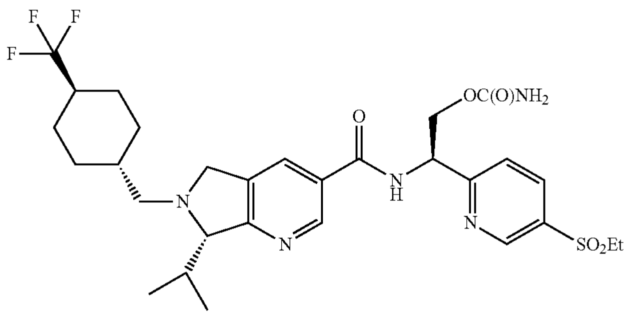 | 1.08 (2 min) 626.2 [M + H]$^+$ | 9.12 (s, 1H), 9.05 (d, J = 2.0 Hz, 1H), 8.33-8.31 (m, 1H), 8.30 (s, 1H), 7.80 (d, J = 8.0 Hz, 1H), 5.62 (t, J = 5.6 Hz, 1H), 5.18-5.14 (m, 1H), 4.76-4.71 (m, 2H), 4.62-4.54 (m, 2H), 3.42-3.40 (m, 2H), 3.31 (t, J = 7.6 Hz, 2H), 2.56-2.54 (m, 1H), 2.22-2.19 (m, 1H), 2.08-2.05 (m, 5H), 1.47 (q, J = 12.4 Hz, 2H), 1.34 (d, J = 6.8 Hz, 3H), 1.28 (t, J = 7.2 Hz, 3H), 1.28-1.26 (m, 2H), 1.12 (d, J = 6.0 Hz, 3H). | | A1, B5, C1 Carbamate formation performed by the prcedure described in Example 2, Step 4. |
| 11 | 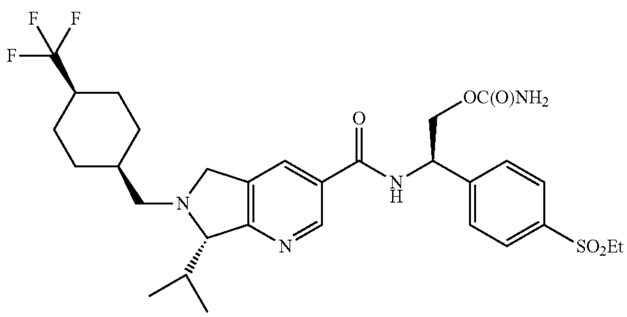 | 0.651 (1.5 min) 625.1 [M + H]$^+$ | 9.08 (s, 1H), 8.25 (s, 1H), 7.92 (d, J = 8.0 Hz, 2H), 7.73 (d, J = 8.4 Hz, 2H), 5.52 (t, J = 6.8 Hz, 1H), 5.15-5.05 (m, 1H), 4.80-4.70 (m, 1H), 4.42 (d, J = 6.4 Hz, 2H), 3.45-3.35 (m, 3H), 3.21 (q, J = 7.2 Hz, 2H), 2.55-2.45 (m, 1H), 2.30-2.20 (m, 2H), 1.79-1.65 (m, 9H), 1.30 (s, 3H), 1.21 (t, J = 7.2 Hz, 3H), 1.07 (s, 3H). | | A2, B1, C1 Carbamate formation performed by the procedure described in Example 2, Step 4. |
| 12 | 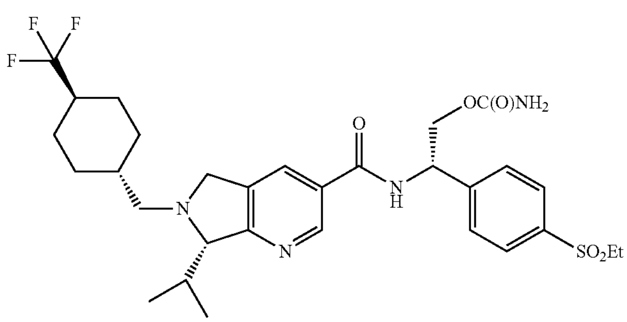 | 0.658 (1.5 min) 625.1 [M + H]$^+$ | 9.36 (d, J = 8.0 Hz, 1H), 9.08 (s, 1H), 8.26 (s, 1H), 7.93 (d, J = 8.4 Hz, 2H), 7.73 (d, J = 8.0 Hz, 2H), 5.52 (t, J = 6.8 Hz, 1H), 5.15-5.10 (m, 1H), 4.75-4.65 (m, 1H), 4.42 (d, J = 6.8 Hz, 2H), 3.45-3.35 (m, 3H), 3.21 (q, J = 7.2 Hz, 2H), 2.55-2.45 (m, 1H), 2.19-1.95 (m, 6H), 1.49-1.40 (m, 3H), 1.31 (d, J = 4.8 Hz, 3H), 1.21 (t, J = 7.2 Hz, 5H), 1.09 (d, J = 6.0 Hz, 3H). | | A1, B1, C1 Carbamate formation performed by the procedure described in Example 2, Step 4. |
| 13 | 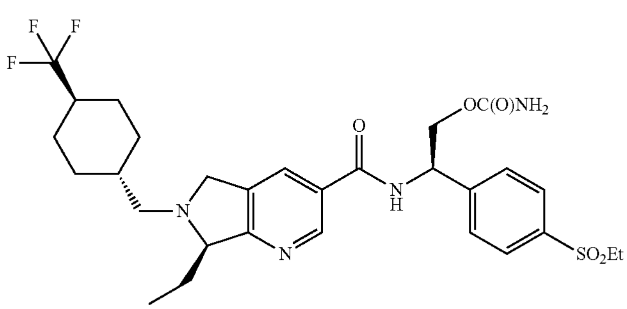 | 0.614 (1.5 min) 611.1 [M + H]$^+$ | 9.36 (d, J = 7.6 Hz, 1H), 9.05 (s, 1H), 8.24 (s, 1H) 7.91 (d, J = 8.4 Hz, 2H), 7.72 (d, J = 8.4 Hz, 2H), 5.52-5.49 (m, 1H), 5.05-5.01 (m, 2H), 4.80-4.69 (m, 1H), 4.41 (d, J = 6.4 Hz, 2H), 3.35-3.30 (m, 2H), 3.20 (q, J = 7.2 Hz, 2H), 2.21-1.99 (m, 8H), 1.46-1.22 (m, 7H), 1.20 (t, J = 7.2 Hz, 3H). | −75.39 | A1, B1, C1 Carbamate formation performed by the procedure described in Example 2, Step 4. |

TABLE 1-continued

| Cpd. No. | Structure | LC/MS (tR, method, m/z) | $^1$H NMR (CD$_3$OD) | $^{19}$F NMR (CD$_3$OD) | Intermediate Components |
|---|---|---|---|---|---|
| 14 | (structure with CF$_3$-cyclohexyl-CH$_2$-pyrrolopyridine-C(O)NH-CH(aryl-SO$_2$Et)-CH$_2$-OCH$_2$COOH, isopropyl) | 0.639 (1.5 min) 640.1 [M + H]$^+$ | 9.21 (s, 1H), 8.33 (s, 1H), 7.91 (d, J = 8.0 Hz, 2H), 7.74 (d, J = 8.0 Hz, 2H), 5.40 (t, J = 5.6 Hz, 1H), 5.15 (d, J = 16.4 Hz, 1H), 4.73 (d, J = 14.8 Hz, 1H), 4.20 (s, 2H), 3.98-3.94 (m, 2H), 3.41-3.37 (m, 2H), 3.22 (q, J = 7.2 Hz, 2H), 2.56-2.52 (m, 1H), 2.24-1.96 (m, 6H), 1.50-1.09 (m, 14H). | −75.42 | A1, B4, C1 Hydrolysis of methyl ester performed after reductive amination |
| 15 | (analogous structure with OCH$_3$) | 0.673 (1.5 min) 596.1 [M + H]$^+$ | 9.25 (d, J = 7.6 Hz, 0.24H), 9.07 (s, 1H), 8.25 (s, 1H), 7.90 (d, J = 8.4 Hz, 2H), 7.71 (d, J = 8.8 Hz, 2H), 5.45-5.42 (m, 1H), 5.15-5.05 (m, 1H), 4.75-4.65 (m, 1H), 3.82-3.74 (m, 2H), 3.41 (s, 3H), 3.35-3.30 (m, 2H), 3.21 (q, J = 7.6 Hz, 2H), 2.55-2.45 (m, 1H), 2.21-1.95 (m, 6H), 1.49-1.39 (m, 2H), 1.27 (d, J = 6.8 Hz, 3H), 1.25-1.23 (m, 3H), 1.21 (t, J = 7.2 Hz, 3H), 1.09 (d, J = 6.8 Hz, 3H). | | A1, B2, C1 |
| 16 | (analogous structure with OC(O)NH$_2$) | 0.659 (1.5 min) 596.1 [M + H]$^+$ | 9.24 (d, J = 7.6 Hz, 1H), 9.08 (s, 1H), 8.26 (s, 1H), 7.90 (d, J = 8.8 Hz, 2H), 7.71 (d, J = 8.4 Hz, 2H), 5.45-5.43 (m, 1H), 5.15-5.05 (m, 1H), 4.75-4.65 (m, 1H), 3.82-3.75 (m, 2H), 3.55-3.45 (m, 2H), 3.41 (s, 3H), 3.21 (q, J = 7.6 Hz, 2H), 2.55-2.45 (m, 1H), 2.35-2.25 (m, 2H), 1.81-1.65 (m, 9H), 1.30 (d, J = 6.8 Hz, 3H), 1.21 (t, J = 7.2 Hz, 3H), 1.08 (d, J = 6.4 Hz, 3H). | | A1, B1, C1 Carbamate formation performed by the procedure described in Example 2, Step 4. |

Biological Assays

Radio-Ligand RORγ Binding Assay (Assay 1)

Compounds of the present invention were tested for ability to bind to RORγ in a cell-free competition assay with commercially available radio-ligand (RL), 25-hydroxy [26,27-$^3$H]-cholesterol (PerkinElmer, Cat. # NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy [26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. # RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. # T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and K$_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds of the present invention were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. # TIB-152). A reporter plasmid was constructed by inserting 5 repeats of the ROR Response Element (RORE) AAAGTAGGTCA (SEQ ID NO:1) into a commercially available promoterless plasmid pNL1.3[secN-luc] (Promega, Cat. # N1021) using KpnI and HindIII restriction sites. The expression plasmid for RORγt was purchased (GeneCopoeia, Cat. # EX-T6988-MO2). Jurkat cells (30 million cells) were transfected with 11 μg of EX-T6988-MO2 and 26 μg of the reporter plasmid in OptiMEM® media using Lipofectamine® LTX and Plus™ reagents (Life Technologies, Cat. #15338-100). After 5-6 hr incubation at 37° C./5% $CO_2$, the cells were collected, resuspended in phenol-red free RPMI media containing 10% (v/v) delipidated FBS (Hyclone, Cat. # SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% $CO_2$ for 16-18 hr. Luciferase activity in the conditioned supernatants was determined with NanoGlo® assay reagents (Promega, Cat.# N1130). Percent inhibition values were calculated based on the fully inhibited and non-inhibited (DMSO) controls, and the values were regressed against concentrations of the tested compounds to derive IC50 values using a four-parameter non-linear fitting model.

Human Whole Blood Assay (Assay 3)

Compounds of the invention were tested in the human whole blood assay to measure their effects on IL-17A production as determined by cytokine secretion into 50% blood/media supernatant. Mixtures of sodium heparinized whole blood (isolated from healthy human donors) and the T cell activator CytoStim, in the presence or absence of compound, were plated in sterilized, tissue culture-treated 24-well plates. Specifically, the mixtures in each well were as follows: (1) 500 μL of whole blood, (2) 250 μL of compound diluted into RPMI-1640 media containing 10% HyClone™ FCS (Thermo Fisher Scientific, Waltham, Mass.), Gibco® Pen/Strep and Gibco® NEAA (Life Technologies, Grand Island, N.Y.), and (3) 250 μL of CytoStim (Miltenyi Biotech, Germany) diluted to a final concentration of 10 μL/mL in complete cell culture medium.

Mixtures were incubated at 37° C./5% $CO_2$ for 48 h, after which, 200 μL of clean supernatant (i.e., no red blood cells) from each well was transferred to a well in a 96-well plate. IL-17A cytokine expression was determined using 25 μL of the transferred supernatant diluted with 25 μL of Diluent 43 from the Human IL-17A V-PLEX™ kit (cat. # K151RFD-4, Meso Scale Discovery, Rockville, Md.). The assay was performed according to the manufacturer's instructions using included reagents. The IL-17A V-PLEX™ plates were read using the Meso Scale Discovery Imager (Model 1200). The levels of IL-17A were extrapolated from a standard curve using a four-parameter non-linear fitting model and expressed as pg/mL. These values were regressed against concentrations of the tested compounds to derive $IC_{50}$ values using a four-parameter non-linear fitting model.

hERG Assay (Assay 4)

Compounds of the invention were tested in vitro against the hERG (human ether-à-go-go-related gene) potassium ion channel (a surrogate for IKr, the rapidly activating delayed rectifier cardiac potassium ion channel).

The buffer was HEPES-buffered physiological saline (HB-PS) solution composed of: 137 mM NaCl, 4.0 mM KCl, 1.8 mM $CaCl_2$, 1 mM $MgCl_2$, 10 mM HEPES, 10 mM glucose, pH adjusted to 7.4 with NaOH, and 0.3% DMSO. Chemicals used in solution preparation were purchased from Sigma-Aldrich (St. Louis, Mo.), unless otherwise noted, and were of ACS reagent grade purity or higher.

HEK (human embryonic kidney) 293 cells were stably transfected with hERG cDNA.

For the patch clamp experiment, onset and steady state inhibition of hERG potassium current was measured using a pulse pattern with fixed amplitudes (depolarization: +20 mV for 2 s; repolarization: −50 mV for 2 s) repeated at 10 s intervals from a holding potential of −80 mV. Peak tail current was measured during the 2 s step to −50 mV. A steady state was maintained for at least 30 seconds before applying compound or positive control (cisapride). Peak tail currents were measured until a new steady state was achieved.

Data acquisition and analyses were performed using the suite of pCLAMP® (ver. 8.2) programs (MDS Analytical Technologies, Sunnyvale, Calif.). Steady state was defined by the limiting constant rate of change with time (linear time dependence). The steady state before and after each compound application was used to calculate the percentage of current inhibited at each concentration.

Concentration-response data were fit to an equation of the following form:

% Inhibition={1−1/[1+([Test]/IC50)N]}*100 where [Test] was the compound concentration, IC50 was the compound concentration at half-maximal inhibition, N was the Hill coefficient, and % Inhibition was the percentage of current inhibited at each compound concentration. Non-linear least squares fits were solved with the Solver add-in for Excel 2003 (Microsoft, WA) and the IC50 was calculated.

The results of assays 1 and 2 are shown in Table 2.

TABLE 2

| Compound # | RORγ Binding Ki Range* (nM) (Assay 1) | RORγt5X IC50 Range* (nM) (Assay 2) |
|---|---|---|
| 1 | +++ | +++ |
| 2 | +++ | +++ |
| 3 | +++ | +++ |
| 4 | +++ | +++ |
| 5 | +++ | + |
| 6 | +++ | + |
| 7 | +++ | ++ |
| 8 | +++ | + |
| 9 | +++ | + |
| 10 | +++ | +++ |
| 11 | +++ | + |
| 12 | +++ | +++ |
| 13 | ++ | |
| 14 | +++ | ++ |
| 15 | +++ | +++ |
| 16 | +++ | +++ |

TABLE 2-continued

| Compound # | RORγ Binding Ki Range* (nM) (Assay 1) | RORγt5X IC50 Range* (nM) (Assay 2) |
|---|---|---|

*+ means >1000 nM; ++ means 100 nM-1000 nM; +++ means <100 nM.

The results of assays 3 and 4 are shown in Table 3.

TABLE 3

| Compound Number | 50% Human Whole Blood Assay IC50, nM* (Assay 3) | hERG Assay (Compound at 3 μM) % Inhibition (Assay 4) |
|---|---|---|
| 1 | +++ | 24.3 |
| 2 | ++ | 38.8 |
| 3 | +++ | 24.3 |
| 4 | +++ | |
| 12 | ++ | 38.8 |
| 15 | +++ | 50 |
| 16 | +++ | 64.9 |

*+ means >200 nM; ++ means 100 nM-200 nM; +++ means <100 nM.

The results of assays 1 to 4 with comparator compounds are shown in Table 4.

TABLE 4

| Comparator Compound | RORγ Binding Ki Range^A (nM) (Assay 1) | RORγt5X IC50 Range^A (nM) (Assay 2) | 50% Human Whole Blood Assay IC50, nM^B (Assay 3) | hERG Assay (Compound at 3 μM) % Inhibition (Assay 4) |
|---|---|---|---|---|
| [structure] | +++ | +++ | | 57.0 |
| [structure] | +++ | +++ | + | 45.4 |

^A+ means > 1000 nM; ++ means 100 nM-1000 nM; +++ means < 100 nM.
^B+ means > 200 nM; ++ means 100 nM-200 nM; +++ means < 100 nM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the Formula:

[structure]

or a pharmaceutically acceptable salt thereof, wherein
$R^2$ is $(C_1-C_3)$alkyl, hydroxy$(C_1-C_3)$alkyl, halo$(C_1-C_3)$alkyl, benzyl, $(C_1-C_3)$alkoxy$(C_1-C_3)$alkyl, tetrahydropyranyl, or —$CH_2$-tetrahydropyranyl;

$Cy^1$ is phenyl or pyridyl, each substituted with $(C_1-C_3)$alkylsulfonyl;

$Cy^2$ is cyclohexyl or tetrahydropyranyl, each optionally substituted with one or more groups selected from halo and halo$(C_1-C_3)$alkyl;

R⁷ is hydrogen, $(C_1-C_3)$alkyl-O—$(C_1-C_3)$alkyl, aminocarbonyl-O—$(C_1-C_3)$alkyl, $(C_1-C_3)$alkylaminocarbonyl-O—$(C_1-C_3)$alkyl, di$(C_1-C_3)$alkylaminocarbonyl-O—$(C_1-C_3)$alkyl, or hydroxycarbonyl$(C_1-C_3)$alkyl-O—$(C_1-C_3)$alkyl; and R⁸ is $(C_1-C_3)$alkyl-O—$(C_1-C_3)$alkyl, aminocarbonyl-O—$(C_1-C_3)$alkyl, $(C_1-C_3)$alkylaminocarbonyl-O—$(C_1-C_3)$alkyl, di$(C_1-C_3)$alkylaminocarbonyl-O—$(C_1-C_3)$alkyl, or hydroxycarbonyl$(C_1-C_3)$alkyl-O—$(C_1-C_3)$alkyl.

2. The compound of claim 1, wherein the compound is of the Formula:

or a pharmaceutically acceptable salt thereof.

3. The compound of claim 2, wherein the compound is of the Formula:

or a pharmaceutically acceptable salt thereof.

4. The compound of claim 3, wherein the compound is of the Formula:

or a pharmaceutically acceptable salt thereof.

5. The compound of claim 4, wherein $R^2$ is $(C_1-C_3)$alkyl.

6. The compound of claim 5, wherein $Cy^2$ is cyclohexyl or tetrahydropyranyl, each substituted with halo$(C_1-C_3)$alkyl.

7. The compound of claim 6, wherein the compound is of the Formula:

or a pharmaceutically acceptable salt thereof, wherein

X is CH or N;
Y is O or $CH_2$;
R⁹ is halo$(C_1-C_3)$alkyl; and
R¹⁰ is $(C_1-C_3)$alkylsulfonyl.

8. The compound of claim 7, wherein the compound is of the Formula:

or a pharmaceutically acceptable salt thereof.

9. The compound of claim 8, wherein the compound is of the Formula:

or a pharmaceutically acceptable salt thereof.

10. The compound of claim 9, wherein R⁹ is $CF_3$; and R¹⁰ is $SO_2Et$ or $SO_2Me$.

11. The compound of claim 10, wherein R⁸ is —$CH_2OCH_3$, —$CH_2OCH_2CH_3$, —$CH_2OC(O)NH_2$, or —$CH_2OCH_2COOH$.

12. The compound of claim 11, wherein R⁸ is —$CH_2OCH_3$.

13. The compound of claim 1, wherein the compound is selected from

-continued
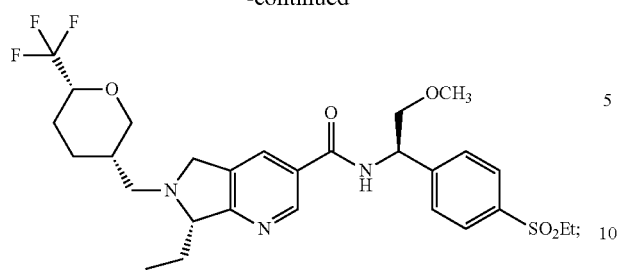
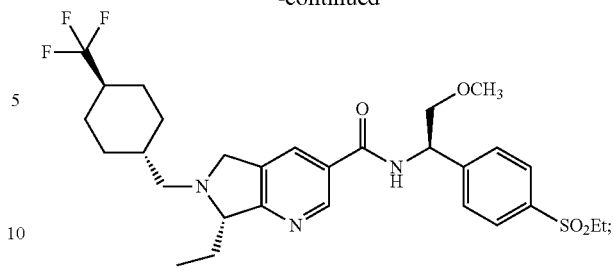
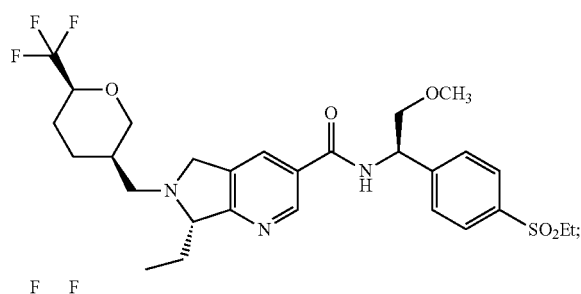
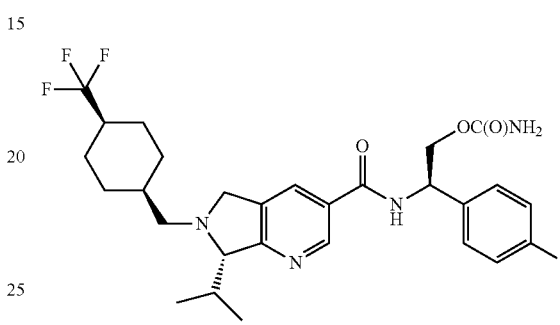
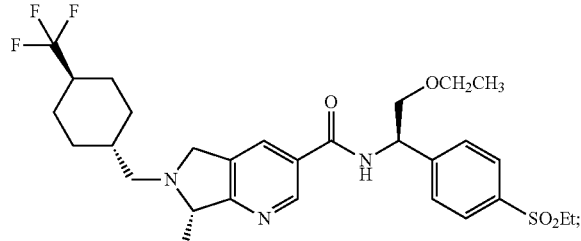
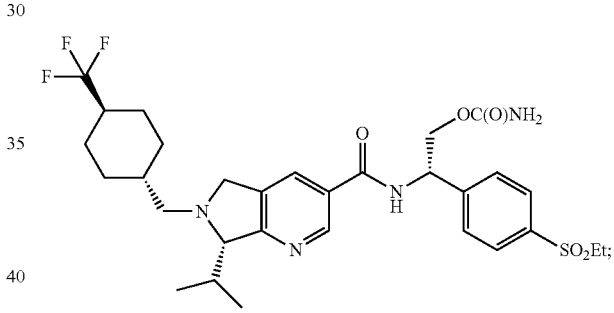
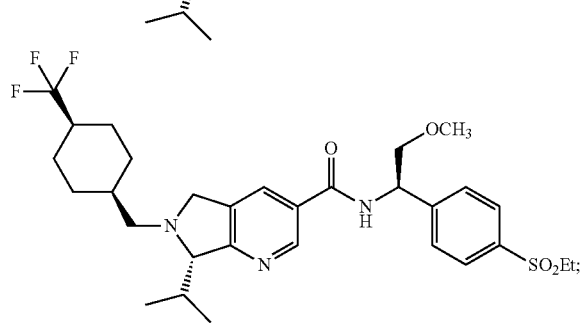
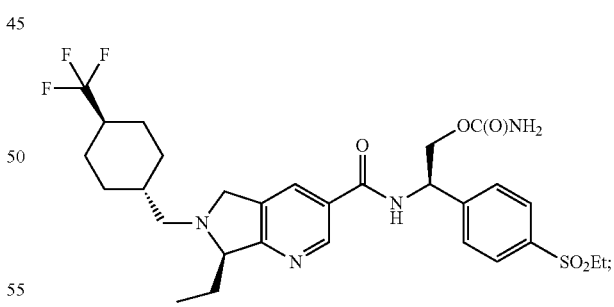
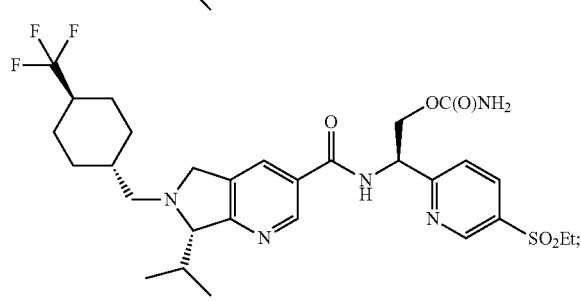
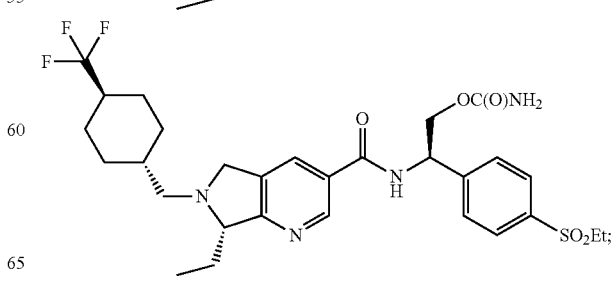

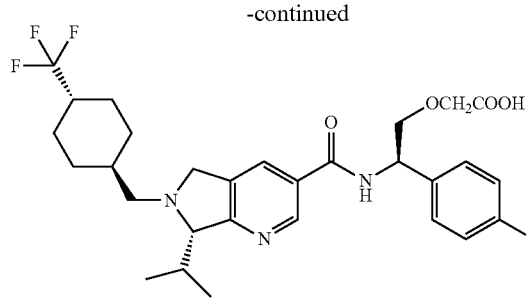

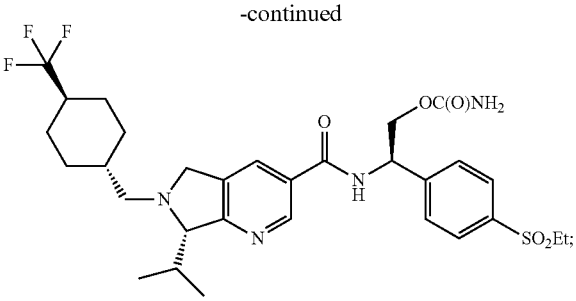

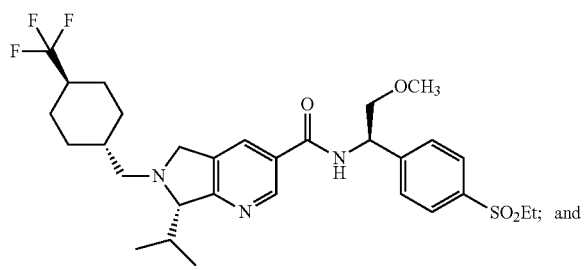

or a pharmaceutically acceptable salt thereof.

14. A pharmaceutical composition comprising a compound of claim 1, or a pharmaceutically acceptable salt thereof, and a pharmaceutically acceptable carrier.

15. A method of treating Crohn's disease, psoriasis, psoriatic arthritis (PsA), inflammatory bowel disease (IBD), rheumatoid arthritis, juvenile rheumatoid arthritis, systemic lupus erythematosus (SLE), multiple sclerosis, ankylosing spondylitis, and asthma in a subject in need thereof, comprising administering to the subject a therapeutically effective amount of a compound according to claim 1, or a pharmaceutically acceptable salt thereof.

* * * * *